US012220705B2

(12) United States Patent
Farshi et al.

(10) Patent No.: US 12,220,705 B2
(45) Date of Patent: Feb. 11, 2025

(54) LOCALIZED DIAGNOSTIC TESTING MODULE

(71) Applicant: Amazon Technologies, Inc., Seattle, WA (US)

(72) Inventors: Jasmin B. Farshi, San Jose, CA (US); Pan Zhang, San Jose, CA (US); Jonathan Barry Hirst, Sunnyvale, CA (US); Babak Ziaie, West Lafayette, IN (US); Bela Incze, Morgan Hill, CA (US); Babar M. Koraishy, Livermore, CA (US)

(73) Assignee: Amazon Technologies, Inc., Seattle, WA (US)

( * ) Notice: Subject to any disclaimer, the term of this patent is extended or adjusted under 35 U.S.C. 154(b) by 0 days.

(21) Appl. No.: 17/703,792

(22) Filed: Mar. 24, 2022

(65) Prior Publication Data

US 2023/0113495 A1 Apr. 13, 2023

Related U.S. Application Data

(60) Provisional application No. 63/254,656, filed on Oct. 12, 2021.

(51) Int. Cl.
| | | |
|---|---|---|
| *C12Q 1/686* | (2018.01) | |
| *B01L 1/00* | (2006.01) | |
| *B01L 3/00* | (2006.01) | |
| *B01L 7/00* | (2006.01) | |
| *G01N 33/487* | (2006.01) | |
| *G16H 10/40* | (2018.01) | |
| *G16H 40/40* | (2018.01) | |

(52) U.S. Cl.
CPC ............... *B01L 3/5029* (2013.01); *B01L 1/50* (2013.01); *B01L 3/5025* (2013.01); *B01L 7/5255* (2013.01); *G01N 33/48771* (2013.01); *G01N 33/48792* (2013.01); *G16H 10/40* (2018.01); *G16H 40/40* (2018.01); *B01L 2200/04* (2013.01); *B01L 2200/0689* (2013.01); *B01L 2200/082* (2013.01); *B01L 2200/10* (2013.01); *B01L 2200/16* (2013.01); *B01L 2300/021* (2013.01); *B01L 2300/027* (2013.01); *B01L 2300/044* (2013.01); *B01L 2300/0609* (2013.01); *B01L 2300/0654* (2013.01); *B01L 2300/0681* (2013.01); *B01L 2300/0832* (2013.01); *B01L 2300/1805* (2013.01); *B01L 2300/1894* (2013.01); *B01L 2400/0478* (2013.01); *C12Q 1/686* (2013.01)

(58) Field of Classification Search
CPC ....... G16H 40/63; C12Q 1/686; B01L 3/5029; B01L 2200/10
See application file for complete search history.

(56) References Cited

U.S. PATENT DOCUMENTS

| | | | |
|---|---|---|---|
| 9,446,418 B2* | 9/2016 | Johns ................ | G01N 35/0099 |
| 11,131,000 B1 | 9/2021 | Lahoud et al. | |
| 2002/0132244 A1* | 9/2002 | Li-Sucholeiki ...... | C12Q 1/6827 435/6.13 |
| 2006/0111620 A1* | 5/2006 | Squilla ..................... | A61B 5/00 600/300 |
| 2006/0246493 A1* | 11/2006 | Jensen ................... | B01L 7/5255 435/6.19 |
| 2010/0032334 A1 | 12/2010 | Weideman | |
| 2016/0025884 A1 | 9/2016 | Difoggio | |
| 2020/0027836 A1 | 1/2020 | Takano et al. | |
| 2021/0285977 A1* | 9/2021 | Tu .......................... | G16H 10/40 |
| 2023/0112431 A1* | 4/2023 | Farshi ................... | G16H 40/40 705/2 |

FOREIGN PATENT DOCUMENTS

| | | | |
|---|---|---|---|
| EP | 2743704 A2 | 6/2014 | |
| EP | 3394293 B1 | 5/2021 | |

OTHER PUBLICATIONS

PCT, "International Search Report and Written Opinion" Application No. PCT/US2022/077921, mailed Jan. 25, 2023, 19 pages.

* cited by examiner

*Primary Examiner* — Young J Kim
(74) *Attorney, Agent, or Firm* — Eversheds Sutherland (US) LLP

(57) ABSTRACT

Systems and methods are disclosed for rapid PCR testing. Example embodiments may include a PCR testing module that includes a housing having a PCR machine disposed therein; a sample input station on the housing, wherein the sample input station is configured to receive a sample collection device (SCD) comprising a biological specimen sample provided by the patient; an SCD processing mechanism configured to transfer a lysed microportion of the biological specimen sample into a PCR sample tube attached to the SCD; at least one mechanism configured to separate the PCR sample tube from the SCD and transfer the PCR sample tube to the PCR machine; and a controller configured to (i) use the PCR machine to conduct a PCR test on contents of the PCR sample tube, and (ii) generate results of the PCR test.

20 Claims, 17 Drawing Sheets

LOCALIZED DIAGNOSTIC TESTING MODULE

CROSS-REFERENCE TO RELATED APPLICATION(S)

This application claims priority to U.S. Provisional Application No. 63/254,656, filed Oct. 12, 2021, the content of which is incorporated herein by reference in its entirety.

BACKGROUND

PCR (polymerase chain reaction) diagnostic testing for various illnesses may be desirable for a number of reasons. Typical PCR tests (e.g., for COVID-19 testing) require that a sample be collected from a person via a nasal swab or saliva, and then the collected sample is transported to a lab, where the sample is processed and placed into a 96-well plate for high volume PCR testing. However, such PCR testing may be cumbersome, time-consuming, and require sample shipping and a centralized lab setup. Systems and methods for rapid PCR testing at a local (e.g., point of care) site may therefore be desired.

Figure 1A:
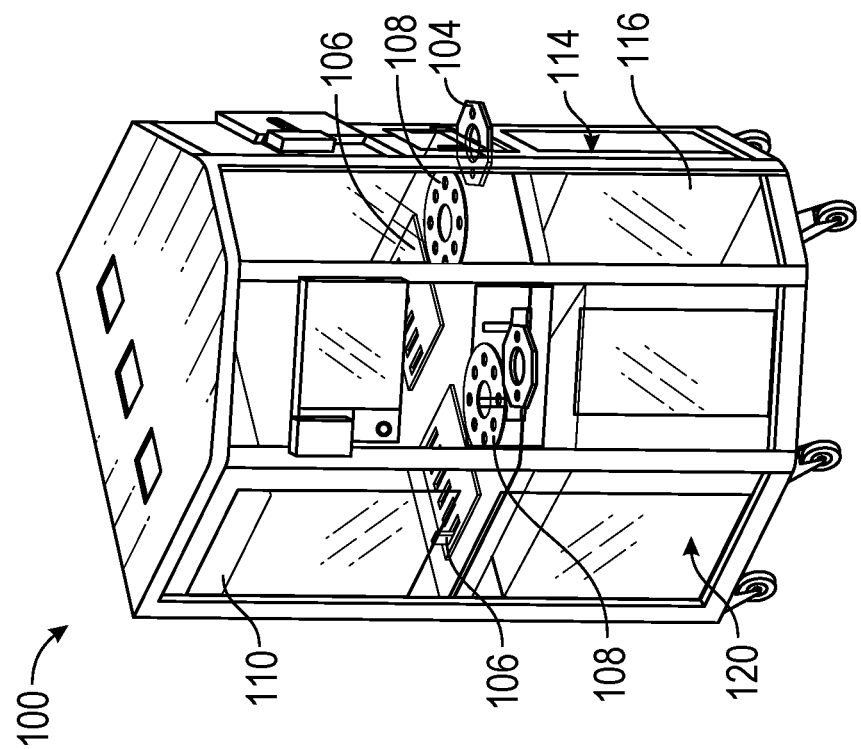
FIGS. 1A-1B are perspective views of an example testing module for localized diagnostic testing according to one embodiment of the present disclosure.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION

Overview

Embodiments of the present disclosure include systems and methods for rapid, local PCR testing. To facilitate this, a local testing module, including PCR configured for use in these systems and methods, has been developed.

In embodiments, the testing module may include a housing having a PCR machine disposed therein; an input station on the cabinet, wherein the input station is configured to receive a sample collection device (SCD) comprising a biological specimen sample; an SCD processing mechanism configured to transfer a lysed microportion of the biological specimen sample into a PCR sample tube; at least one mechanism configured to transfer the PCR sample tube to the PCR machine; and a controller configured to cause the PCR machine to (i) conduct a PCR test on contents of the PCR sample tube, and (ii) generate results of the PCR test.

In particular embodiments, the testing module may be used to diagnose a particular illness at a point of care site or other locations. In embodiments, the testing module performs a PCR test on a sample collected by a sample collection device (SCD) used in conjunction with the testing module. The SCD may be configured for collecting a saliva specimen from the mouth of a patient, or for collecting a nasal mid-turbinate (NMT) specimen, or anterior nasal specimen, from a nostril of a patient. The patient may be a human. The sample may also be collected from an object. These collections may be self-administered by a patient following collection instructions or performed by a trained healthcare provider. The sample collection device may be configured for collecting other biological fluids from a human or non-human mammal. The collected specimen may be referred to herein as a "sample." In embodiments, the sample is placed into the testing module by a patient or other user following instructions or by a trained healthcare provider.

The SCD includes at least a swab and a sample container. In some embodiments, the SCD provided to the testing module may include an attached PCR sample tube. For example, the SCD provided to the patient for receiving the biological specimen may include an SCD having a pre-attached PCR sample tube. In other embodiments, the SCD provided to the testing module may have no PCR sample tube. In those embodiments, the testing module may include mechanisms configured to retrieve a PCR sample tube from a storage rack or other source within the housing and configured to attach the PCR sample tube to the SCD following receipt of the SCD by the testing module. In an alternative embodiment, the PCR sample tube and/or a sample container portion containing the biological specimen sample may be separated from the SCD or from the swab, respectively, prior to the sample being deposited in the testing module.

Once the sample is inserted in the testing module, the testing module will extract the biological specimen sample, lyse it, mix it with water and appropriate reagents (e.g., a lyophilized master mix), and present this mixture in a PCR sample tube, which in particular embodiments is attached to the SCD. The sample tube is then processed in a PCR machine contained within the testing module. In some embodiments, the testing module is configured to test multiple samples in parallel or simultaneously. In some embodiments, the testing module can test up to 200 samples simultaneously. In embodiments, the testing module inactivates the sample to render it non-infectious before testing it. In some embodiments, the testing module includes a continuous PCR system.

In some embodiments, the PCR machine performs a PCR test on the sample to amplify genetic material of interest. It is understood that any method known in the art for amplifying genetic material may be used, including standard PCR, qPCR, RT-PCR, RT-qPCR, and hot start PCR. In embodiments, the testing module may have more than one PCR machine and be able to perform more than one type of PCR. In some embodiments, the PCR machine runs a PCR test of the PCR sample tube contents to determine whether the lysed biological fluid sample includes a particular RNA, such as one indicative of a particular pathogen. For example, the RNA may be one indicative of the SARS-CoV-2 virus. Accordingly, the test module may generate PCR test results that enable diagnosis of one or more particular diseases or illnesses.

The testing modules described herein facilitate rapid PCR testing at a point-of-care site or other locations of convenience to patients, office workers, travelers, etc. In embodiments, the testing module comprises one or more user interfaces with an interactive screen. Test results may appear on the screen and/or be sent to a patient via email, text message, app, or webpage.

In some particular embodiments, the testing module includes a housing having a PCR machine contained therein; a sample input station on the cabinet, wherein the sample input station is configured to receive an SCD comprising a biological specimen sample provided by the patient; an SCD processing mechanism configured to transfer a lysed microportion of the biological specimen sample into a PCR sample tube attached to the SCD; at least one mechanism, e.g., robotic arms and actuators, configured to separate the PCR sample tube from the SCD and transfer the PCR sample tube to the PCR machine; and a controller configured to use the PCR machine to conduct a PCR test on contents of the PCR sample tube, and to generate results of the PCR test.

In embodiments, the testing module also may include an interface on the housing, e.g., the main cabinet, for a user to interact with the testing module. The interface may be configured to accept input associated with conducting one or more PCR tests. In some embodiments, the testing module may include two or more such user interfaces.

In embodiments, the testing module may include a first scanner configured to read a first machine-readable code on the SCD and a second scanner configured to read a second machine-readable code on the PCR sample tube. Examples of the first and second machine-readable code include barcodes, QR codes, and the like. The first and second codes may be the same as or different from one another. The first scanner may be configured to read a machine-readable code on the SCD received by, or to be received by, the sample input station.

In embodiments, the testing module includes (i) an oven or other heater configured to thermally lyse the biological specimen sample in the SCD received by the sample input station, and (ii) a sonicator or other mixing device to mix the lysed microportion of the biological specimen sample with other materials in the PCR sample tube attached to the SCD. The other materials may include water, a master mix, and any other reagents needed for the PCR test.

In embodiments, the testing module includes a sealing machine configured to seal a PCR sample tube before it is transferred to the PCR machine. For example, the sealing machine may apply a foil or polymeric film over the opening of the PCR sample tube. In other embodiments, the PCR sample tubes may be sealed with a closure, such as a cap or plug. Such sealing machines, films, and closures are known in the art.

In embodiments, the PCR machine may include a continuous PCR system which includes a conveyor system for moving a plurality of received PCR sample tubes through heating and cooling zones within the PCR machine. The PCR machine may include a sample scanner configured to read a bar code on each of the plurality of PCR sample tubes. The continuous PCR system may include an array of laser diodes and photodetectors to detect the fluorescent intensity in each of the plurality of PCR sample tubes as the PCR sample tubes are conveyed through thermal cycles.

In some embodiments, the testing module is configured for use with particular SCDs. For example, the SCD may include (i) a swab stick configured for collecting a saliva sample, or a nasal or throat surface sample, from a patient; and (ii) a sample container configured to receive the swab stick and to separate a bulk quantity of the sample from the swab stick for containment in a bulk collection chamber for lysing, which is located with the sample container. In particular embodiments, the sample container is configured to meter a microportion of the lysed sample into a PCR sample tube releasably attachable to the sample container.

In some embodiments, the PCR machine performs a PCR test on the sample to amplify genetic material of interest. It is understood that any method known in the art for amplifying genetic material may be used, including standard PCR, qPCR, RT-PCR, RT-qPCR, and hot start PCR. In embodiments, the testing module may have more than one PCR machine, and be able to perform more than one type of PCR. In some embodiments, the PCR machine runs a PCR test of the PCR sample tube contents to determine whether the lysed biological fluid sample includes a particular RNA, such as one indicative of a particular pathogen. For example, the RNA may be one indicative of the SARS-CoV-2 virus. Accordingly, the test module may generate PCR test results that enable diagnosis of one or more particular diseases or illnesses.

Figure 2:
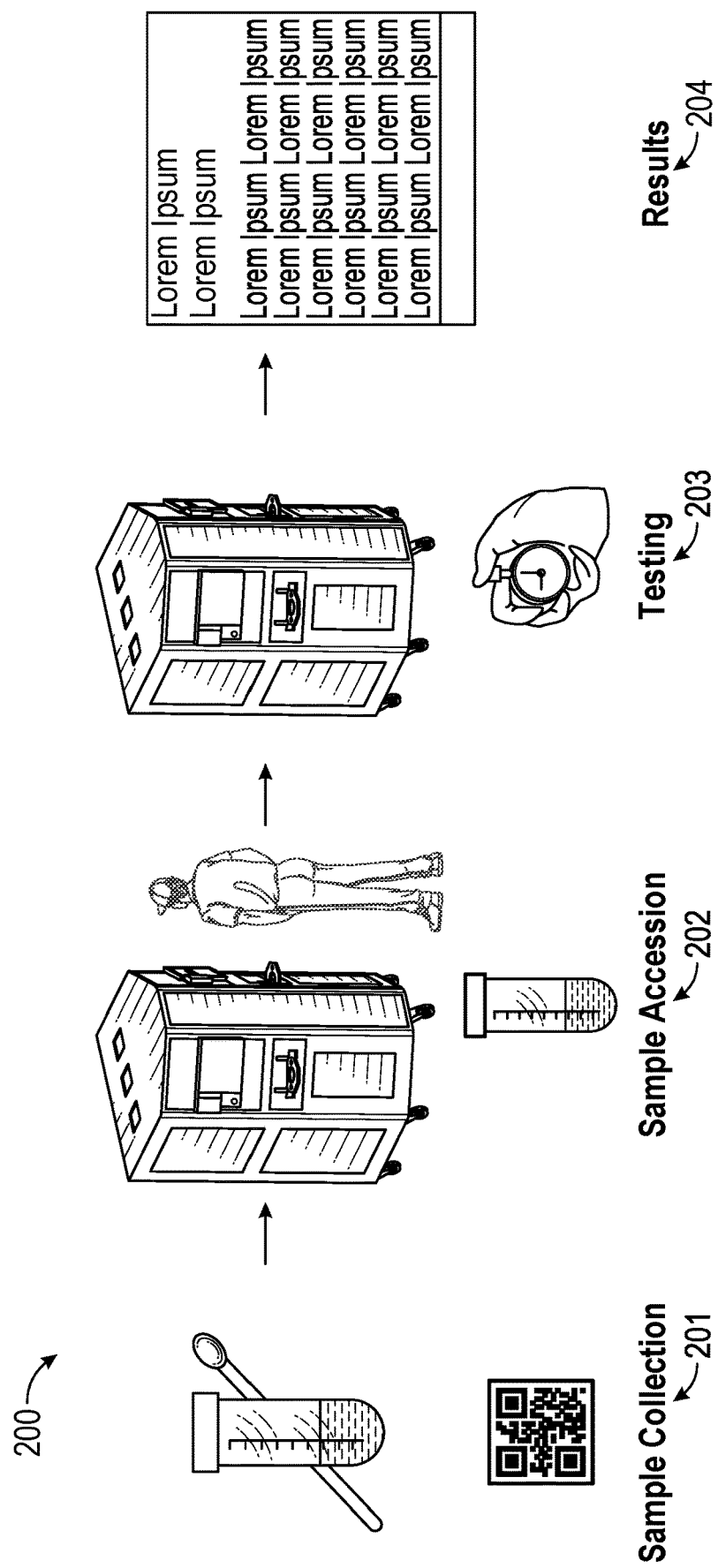
FIG. 2 is an example process flow of a consumer (patient) experience using a localized diagnostics testing system.

The testing modules described herein facilitate rapid, local PCR testing, for example, at a point of care site, and rapidly reporting the test results to the patient and others as appropriate. FIG. 2 depicts an example process flow 200 of the consumer (e.g., user or patient) experience. The process flow 200 may consist of several stages, including the Sample Collection 201, Sample Accession 202, Sample Testing 203, and Results 204 Stages.

During the Sample Collection Stage 201, the SCD is distributed to patients, such as employees, guests, or consumers. Each SCD has an affixed barcode or QR code to identify the specific SCD and associate it with a particular patient. The SCD is scanned, for example, using a badge or an application. The SCD is used to collect a biological sample from a patient, as described herein. The patient may self-collect the sample or another person may assist the patient in collecting the sample. Once the sample is collected, the sample is deposited into the system during the Sample Accession Stage 202. Specifically, the SCD and, therefore, the sample are placed into the testing module, as further described below.

Referring again to FIG. 2, once the sample enters the testing module, the Testing Stage 203 begins. During the Testing Stage 203, the sample is tested using PCR, for example, to identify a particular agent in the biological sample. For example, the agent may be RNA indicative of the SARS-CoV-2 virus. The testing module may run at a defined frequency and test up to 192 samples an hour. The Testing Stage 203 may last approximately 30 minutes, after which it reports results. During the Results Stage 204, the results of the Testing Stage 203 are reported to the patient/user. The results may indicate that the patient is positive or negative to a particular illness. In embodiments, the results may be reported on a screen attached to the testing module. In embodiments, the results may be reported to the user via an app, email, and/or text message. The results may also be reported to a third party (as permitted and consistent with patient privacy regulations), such as appropriate healthcare authorities or the patient's doctor.

Figure 4:
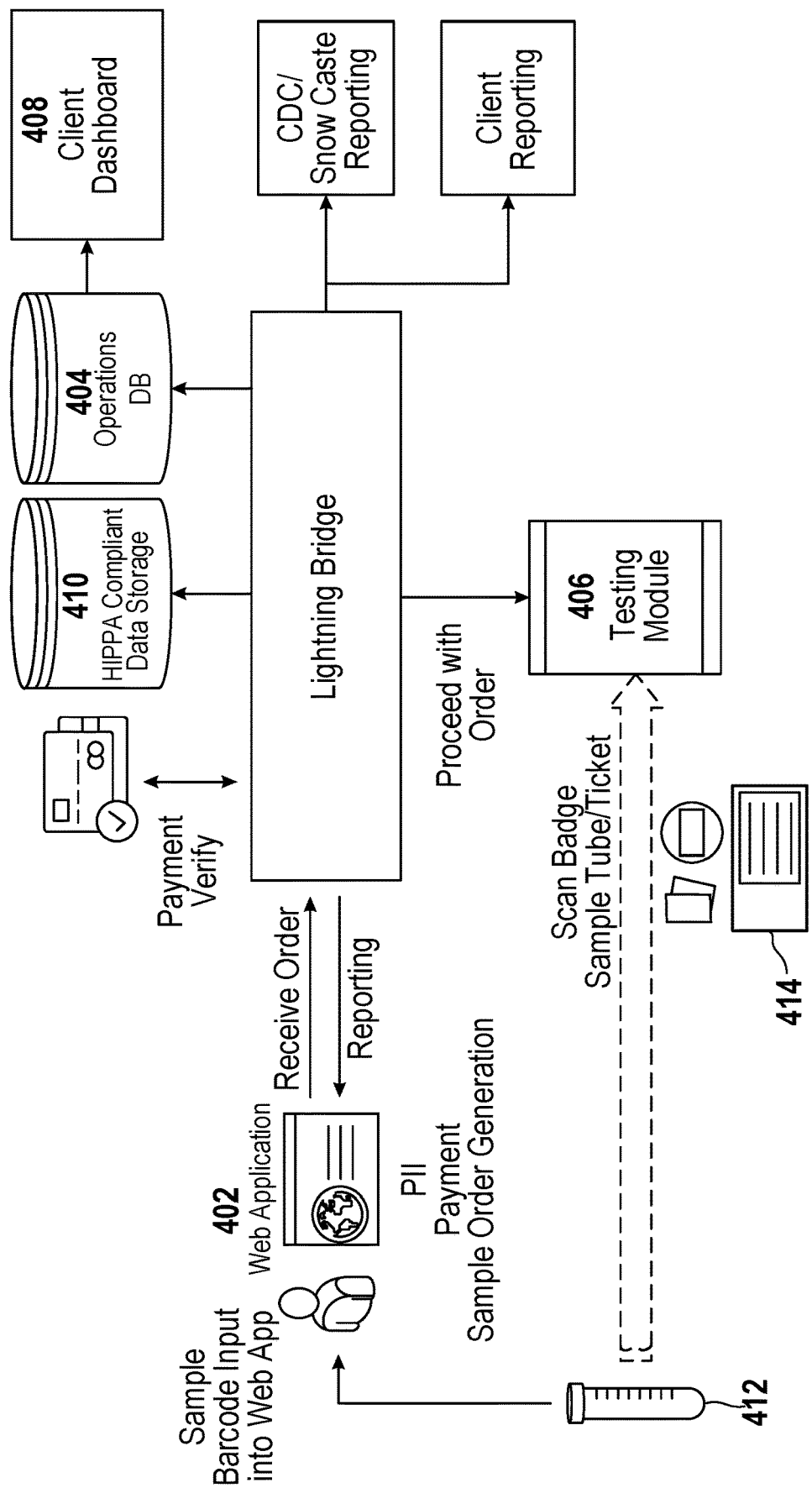
FIG. 4 is an example process flow for managing data in a localized diagnostics testing system, according to one embodiment of the present disclosure.

FIG. 4 is an example process flow for managing data in the local diagnostics testing system. Embodiments may include a secure tunnel that can be utilized to intake order information from a web application 402, store some of the info into one or more databases 404, 410, and complete the data exchange between various testing modules 406, databases 404, user intake portal, health reporting, result dashboard, and/or system monitoring services. Specifically, a sample's 412 barcode input may be entered via web app 402 or by scan of a badge 414 (e.g., a corporate ID badge) or ticket by the testing module 406. Once the order is received payment may be requested and verified, for example, by communications with a payment processor as known in the art. The results of the PCR test may be stored in a HIPPA-compliant database 410 and reported to the client and/or appropriate authorities, such as the Centers for Disease Control (CDC). A client (e.g., an owner or administrator of the testing module) may enter information and/or receive operational information (e.g., testing module status, usage history, consumables inventory within the testing module, etc.) through a client dashboard 408.

Use of the test modules described herein may include one or more of the following operations: 1) a patient performs identification and financial transaction on the testing module; 2) the testing module dispenses an packaged SCD comprising a unique barcode, QR code, or other identifier associated with the patient in accordance with the identification and financial transaction; 3) the patient opens the package and withdraws the SCD kit; 4) the testing module presents instructions to the patient for use of the SCD kit; 5) the patient inserts an absorbent swab portion of the swab stick part of the SCD kit in their mouth or nose to collect a suitable biological specimen; 6) the patient inserts the swab stick into the sample container; and 7) the patient inserts the combined swab stick and sample container, i.e., the SCD, into the testing module. The testing module processes SCD and then discards it following separation of the PCR sample tube.

One or more illustrative embodiments of the disclosure have been described above. The above-described embodiments are merely illustrative of the scope of this disclosure and are not intended to be limiting in any way. Accordingly, variations, modifications, and equivalents of the embodiments disclosed herein are also within the scope of this disclosure. The above-described embodiments and additional and/or alternative embodiments of the disclosure will be described in detail hereinafter through reference to the accompanying drawings.

Illustrative Embodiments and Use Cases

Figure 1B:
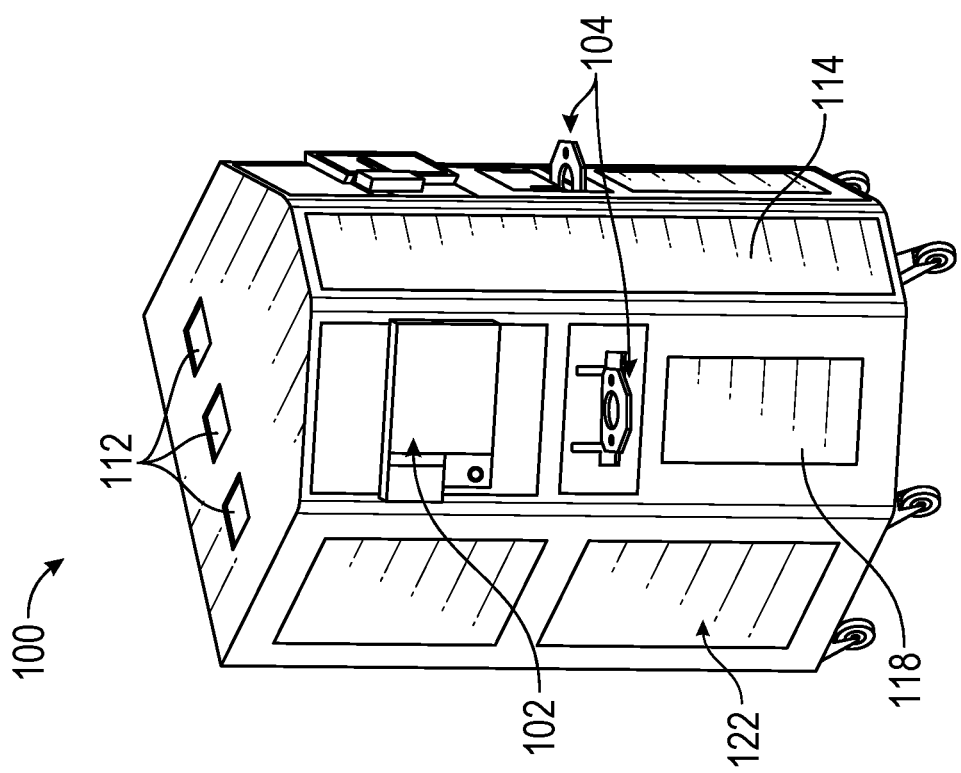

In some embodiments, the testing module is located at a point of care site such as an office building, medical facility, or other commercial building. FIGS. 1A-1B depict an example testing module 100. FIG. 1A shows an external view of the testing module 100, and FIG. 1B is a partially transparent view to show some of the internal component of the testing module 100.

The testing module includes a housing, or main cabinet, 114 which comprises an enclosure for PCR machines 106. The testing module 100 may include one or more patient interfaces 102 for the user/patient to use the testing module. The user interface 102 may comprise an interactive screen. The user interface 102 may assist the user in various ways, including but not limited to providing instruction to the user, accepting payment for the test, identification of the user, and/or output of test results, including prior test results. Some or all of these user interface functions may alternatively or additionally be provided to the user via email, text message, app, or webpage.

The PCR testing module 100 includes one or more sample input stations 104 for receiving the SCD. The testing module 100 includes one or more processing units 108 for handling the SCDs and PCR sample tubes. The processing unit 108 may include: (i) a barcode scanner configured to read a barcode on the SCD to be received by the sample input station; (ii) an oven or other heater configured to thermally lyse the saliva sample in the SCD received by the sample input station; (iii) an SCD processing mechanism configured to transfer a lysed microportion of the sample in a PCR sample tube attached to the SCD received by the sample input station; a sonicator configured to ultrasonically mix the lysed microportion of the sample, the water, and the lyophilized master mix in the PCR sample tube attached to the SCD. Suitable scanners, heaters, and sonicators are known in the art.

The testing module 100 also may include one or more robotic manipulators configured to (i) separate the PCR sample tube from the SCD and discard the SCD into the biohazard waste bin 116 within the cabinet 114, (ii) seal the separated PCR sample tube, and (iii) transfer the sealed PCR sample tube to the PCR machine 106. The testing module 100 also may include a controller configured to operate the PCR machine 106.

The testing module 100 may include a consumables storage area in the main cabinet for the biohazard waste bin 116, for collection of used SCDs and PCR sample tubes. Disposal bay doors 118 may allow for access to the consumable storage area. The testing module 100 may also include an electrical cabinet 120, which may be accessed through a maintenance access door 122. The testing module 100 also includes a HEPA filter unit 110 and exhaust ports 112.

In operation, once the SCD is inserted in the testing module 100, the testing module will interact with the SCD, extract the biological specimen sample, lyse it, mix it with water and lyophilized master mix, and present this mixture in the attached PCR sample tube, which in particular embodiments, is a standard 0.2 ml sample tube, as known in the art. The testing module 100 may separate the sample tube and/or sample container containing the sample from the SCD within the device; alternatively, the sample tube and/or sample container containing the sample may be separated from the SCD prior to being deposited in the testing module 100. The sample container of the SCD and the PCR sample tube will then be separated, with the sample tube then being sealed and processed in a PCR machine 106 while the SCD is discarded.

In one embodiment, SCD 300 is processed by a testing module after a patient uses the swab stick to collect a sample, places the swab stick in the sample container, and then deposits the swab stick and the sample container into the testing module. The testing module then may load a PCR sample tube, e.g., from a storage rack, and dispense a predetermined quantity of water (e.g., ~15 uL) into the sample tube. The water may rehydrate the lyophilized master mix in the sample tube. The testing module then may attach the sample tube to the SCD as described above. The testing module then may depress the swab plunger to compress the absorbent swab so that saliva is released into the bulk saliva collection chamber. The testing module may stop pressing plunger after translating a programmed distance. The testing module then may apply thermal energy to the sample container effectively to heat the bulk saliva to 95° C. for several minutes and lyse the saliva sample. The testing module then may continue to depress the plunger, which in return causes the metering piston (i.e., piercing plunger) to translate into the micro sample tube to eject 5 µl of the lysed saliva sample into the attached PCR sample tube. The testing module then applies ultrasonic energy to mix together the components in the PCR sample tube. Then, the testing module separates the SCD from the PCR sample tube and then seals the sample tube, e.g., with a film or foil material known in the art. The testing module then may place the PCR sample tube in a PCR machine and run a PCR test on the same in the PCR sample tube. The testing module may discard the used SCD into a waste receptacle. Once the PCR test is complete, then the testing module may also discard the sample tube into a waste receptacle.

In some embodiments, the SCD used in connection with the testing module may be provided in a two-part kit, which may be sterilized within flexible packaging prior to use. FIG. 3A depicts an example sample collection device (SCD) 300, comprising a first part 302, which includes an absorbent swab 301 mounted on a convenient holder 303, sometimes referred to as a swab stick, and a second part 304, which includes a sample container. The absorbent swab 301 may be inserted in the mouth of a patient to absorb saliva pooled in the mouth. Alternatively, the absorbent swab 301 may be inserted into the nasal cavity. After sample collection, the absorbent swab 301 is inserted into the sample container 304, as illustrated in FIG. 3B.

The sample container 304 has features that enable 1) bulk sample extraction from the swab stick 102; 2) lysis of the bulk sample; 3) and PCR sample tube attachment; and 4) metering of a microsample (~5 µl) of the biological sample from the bulk sample, and transferring the microsample to the PCR sample tube. The PCR sample tube is pre-sealed prior to attachment to the sample container 104 and may contain a lyophilized master mix as known in the art. For example, a suitable lyophilized master mix for use in PCR detection of pathogens in biological samples may include PCR buffer, cofactor (e.g., $MgCl_2$), dNTPs, probes (e.g., dye), and enzymes (e.g. polymerase and reverse transcriptase). In embodiments, primers, the sample, and water are added to the lyophilized master mix. In embodiments, if the testing module is configured to detect only a specific pathogen, the primers may be lyophilized and included in the master mix.

Figure 3B:
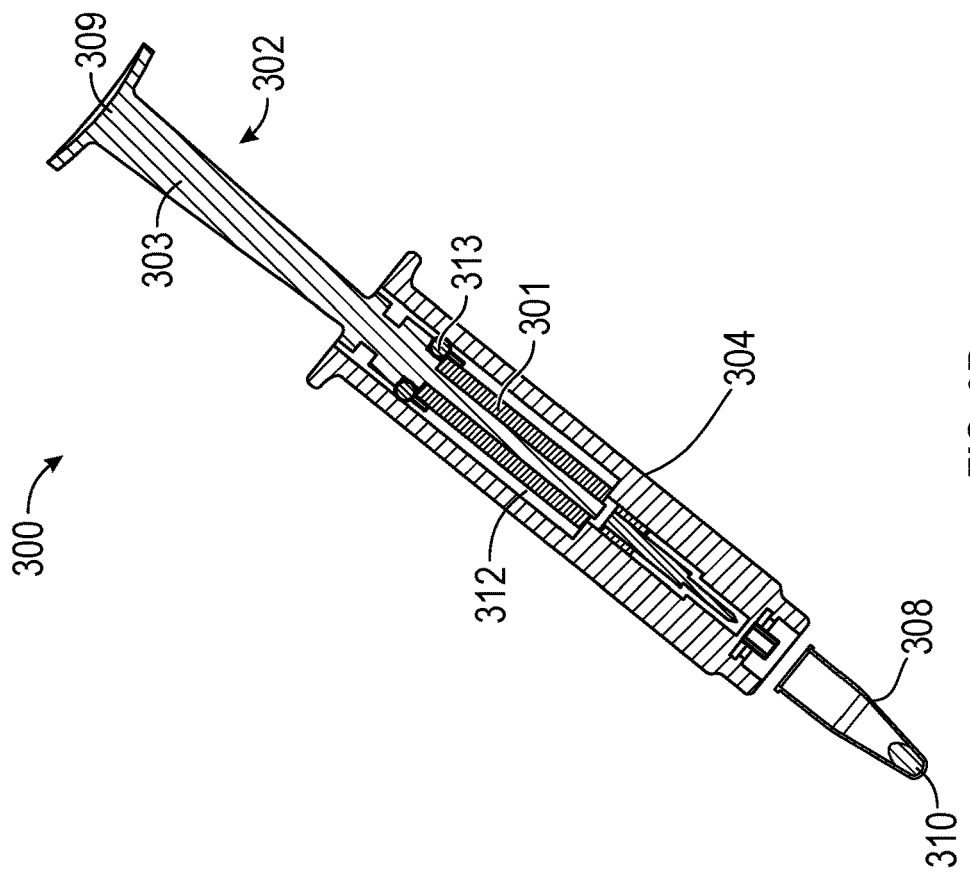
FIG. 3B is a cross-sectional view of an example SCD, according to one embodiment.
Figure 3A:
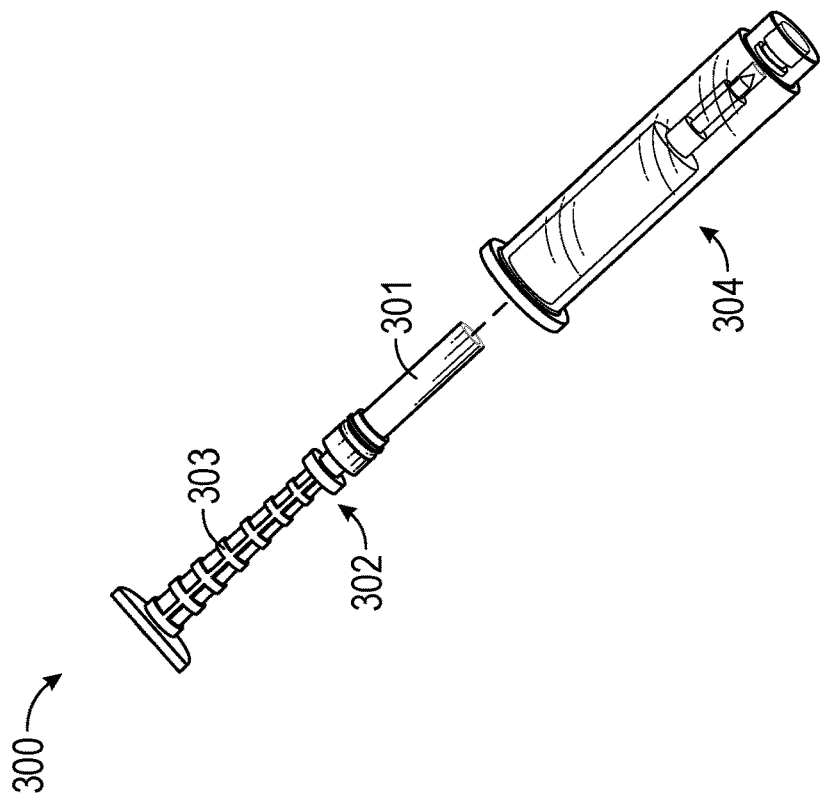
FIG. 3A is perspective view of an example sample collection device (SCD) used in conjunction with a testing module as described herein.

FIG. 3B shows an example SCD 300 with a swab stick 302 inserted into sample container 304, which is configured to be attached to PCR sample tube 308, which is pre-loaded with a lyophilized master mix 310. In embodiments, the lyophilized master mix 310 may include a suitable chemical lysate known in the art. The swab stick 302 includes a plunger 309 that acts as a handle for the patient to hold during collection of a biological specimen and for guiding the absorbent swab 301 into the sample container 304. The swab stick also includes a sealing member 313, which may be an elastomeric material, for forming a fluid tight seal with an interior surface of a swab receiving chamber 312 in the sample container 304. The sealing member 313 may be disposed between the plunger 309 and the absorbent swab 301 and configured to matingly engage with the interior surface of the swab receiving chamber 312.

Figure 3D:
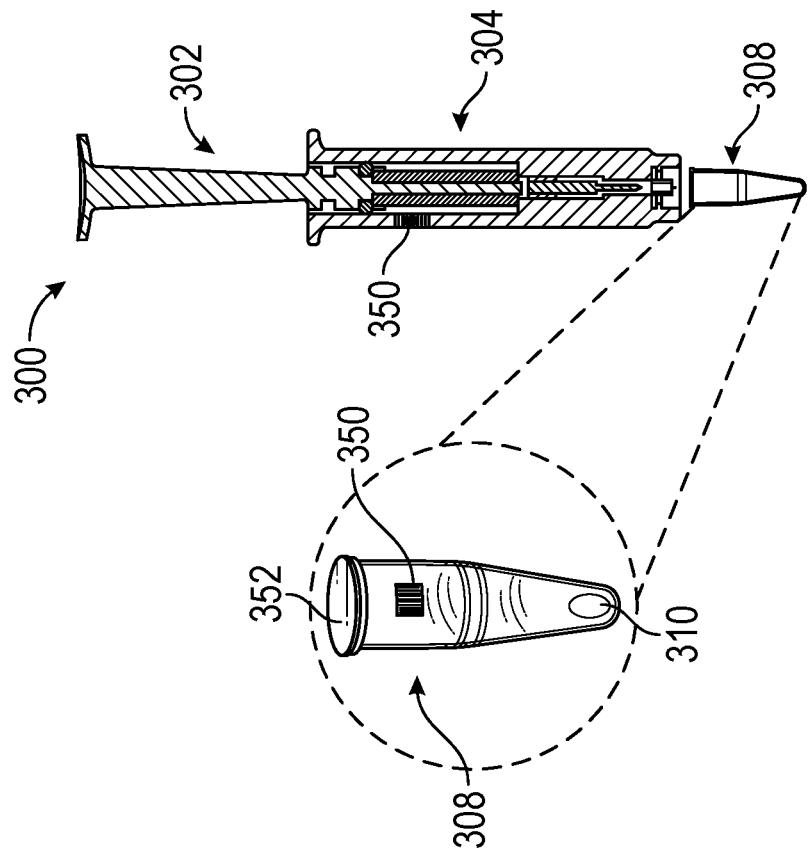
FIG. 3D depicts an example CD and PCR sample tube, which each have a barcode for sample tracking, according to one embodiment.
Figure 3C:
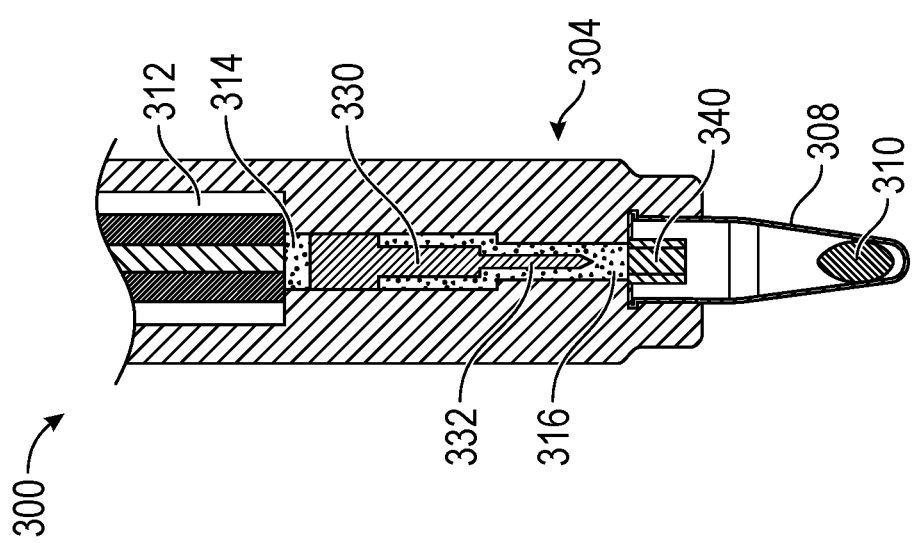
FIG. 3C is close-up, cross-sectional view of a portion of an example SCD with connected sample container, according to one embodiment.

FIG. 3C is a close-up cross-sectional view of part of SCD 300. Sample container 304 is shown with swab chamber 312 having received the saliva swab 301. The swab chamber 312 is in fluid communication with a bulk saliva collection chamber 314, which is configured to receive saliva extracted/transferred from the saliva swab 301. A micro sample chamber 316 is in fluid communication with the bulk saliva collection chamber 314, distal to the swab chamber. The micro sample chamber 316 is dimensioned/configured to hold a selected volume, e.g., about 5 µl, of the saliva transferred from the bulk saliva collection chamber. The selected volume may be referred to as a "microportion," which may be from 1 µl to 10 µl, for example.

The sample container 304, as shown, is releasably attached to a PCR sample tube 308, which contains a lyophilized master mix 310. The attachment may be by frictional engagement. The PCR sample tube attachment may be performed by the testing module after the SCD containing the collected biological specimen has been inserted into the testing module, or the PCR sample tube attachment may be performed by a user before the SCD containing the collected biological specimen is inserted into the testing module. The sample container also includes a projection 340, which is configured to pierce a seal on the top of the PCR sample tube 308 upon the attachment of the PCR sample tube 308 to the sample container 304. The projection 340 includes a through-channel that is in communication with the micro sample chamber 316.

After the initial insertion of the saliva swap into the sample container, the saliva swab may be translated into the swab chamber 312, a first distance that will compress the saliva swab 301 and thereby release collected saliva into the bulk saliva collection chamber 314. After chemical or thermal lysing of the saliva in the bulk saliva collection chamber 314, further downward translation of the saliva swab into the swab chamber 312 a second distance will drive swab plunger 320, which extends from the holder 303, into contact with the metering piston 330 and drive at least part of the metering piston into the micro sample chamber 316, and displace the selected volume of the lysed saliva from the micro sample chamber 316 into the PCR sample tube 308. These translations of the first and second distances are performed in and by the testing module, for example, by the processing unit 108 and/or one or more robotic manipulators.

As shown in FIG. 3D, each SCD 300 and each PCR sample tube 308 includes a unique barcode, QR code, or the like 350. This is used to allow the testing module to properly track/associate a patient's sample with the ultimate results from the PCR test. As shown, the PCR sample tube 308 includes a seal 352, which may be a thin foil or polymeric film, and a master mix 310 contained within the interior space defined by the sample tube walls.

Figure 5B:
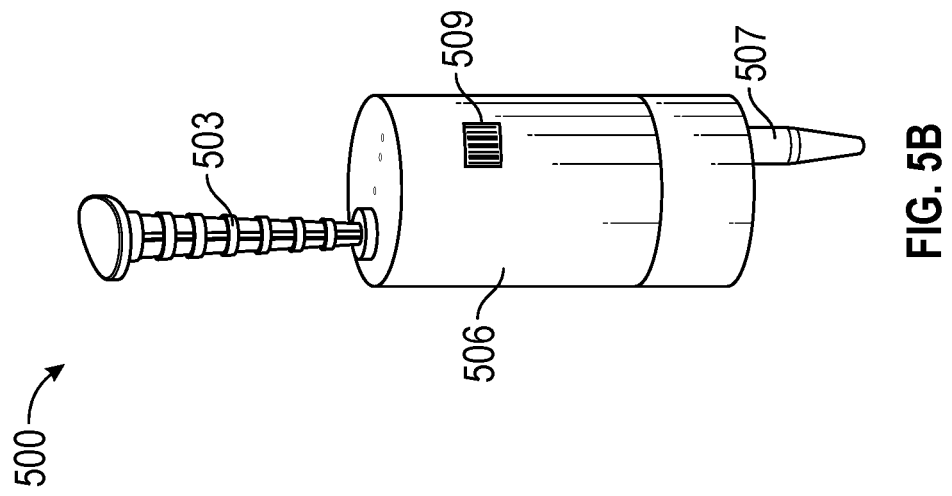
FIGS. 5A-5B are perspective views of an example SCD, according to one embodiment of the present disclosure.
Figure 5A:
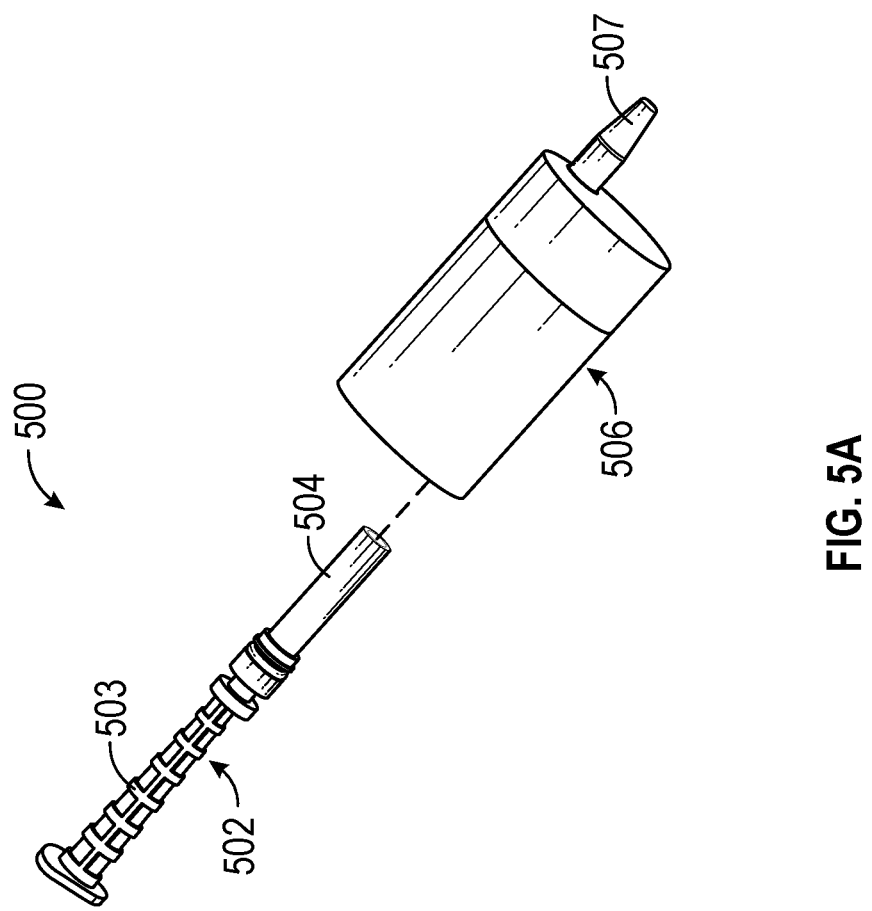

Another embodiment of a sample collection device 500 is illustrated in FIGS. 5A-5F. The SCD 500 includes a swab stick 502, a sample container 506, and PCR sample tube 507. The swab stick 502 comprises a plunger handle 503 and an absorbent swab 504. The absorbent swab may be a saliva swab. The sample container 506 includes a barcode, QR code, or the like 509. In embodiments, the entire SCD 500 as depicted in FIG. 5B is inserted into the testing module.

Figures 5C, 5D:
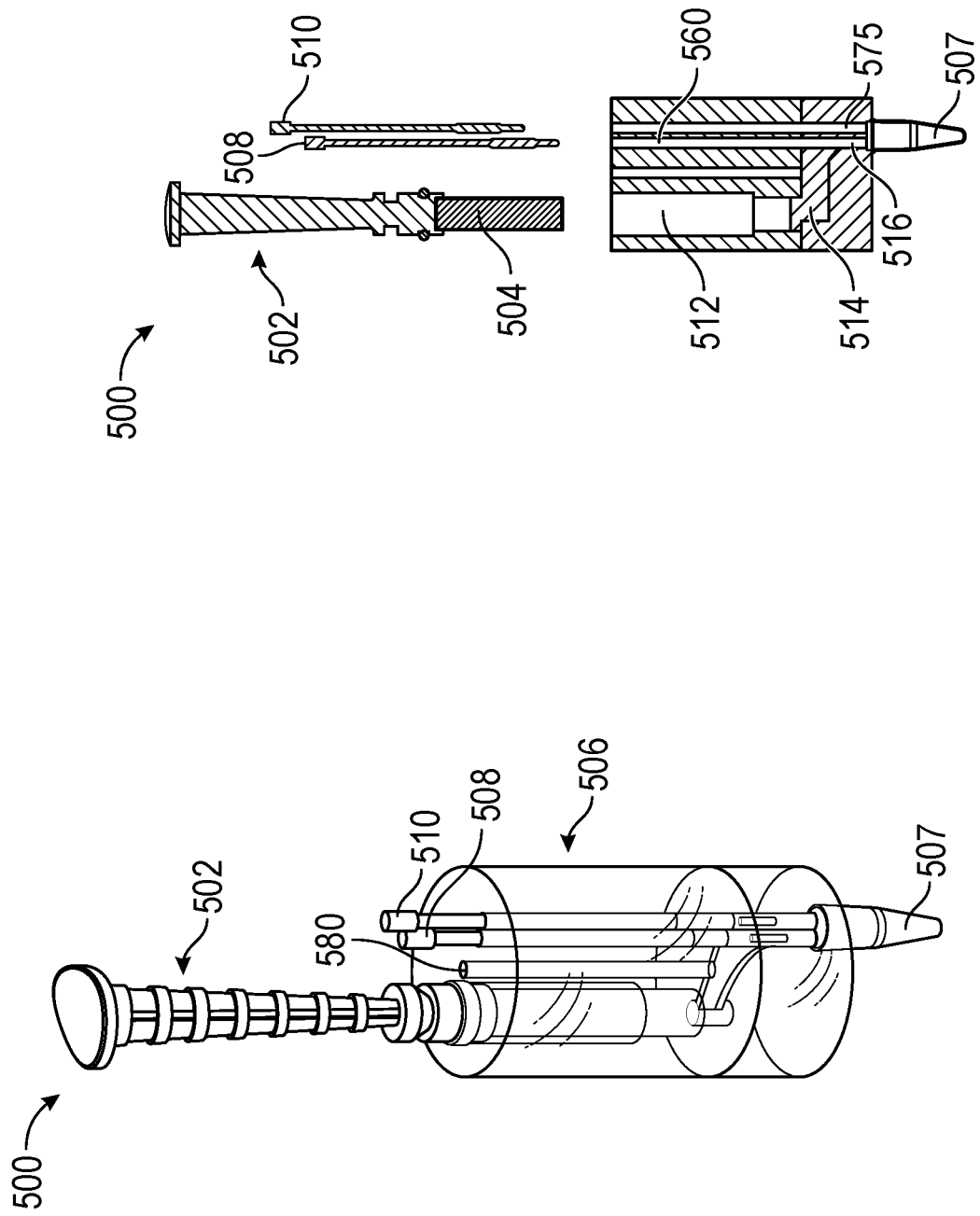
FIG. 5C is a transparent, perspective view of an example SCD, according to one embodiment of the present disclosure.
FIG. 5D is cross-sectional, exploded view of an example SCD, according to one embodiment of the present disclosure.

As shown in FIGS. 5C-5D, the sample container 506 includes swab chamber 512 for received the absorbent swab 504. The top of the sample container 506 includes an opening to access the swab chamber 512, as well as a separate air vent 580 opening and openings to receive a water chamber piston 510 and a metering piston 508. The swab chamber 512 is in fluid communication with a bulk saliva collection chamber 514, which is configured to receive saliva extracted/transferred from the absorbent swab 504. A micro sample chamber 516 is in fluid communication with the bulk saliva collection chamber 514. The micro sample chamber 516 is dimensioned/configured to hold a selected volume, e.g., about 5 μl, of the saliva from the bulk saliva collection chamber. The selected volume may be a microportion, which may be from 1 μl to 10 μl, for example.

The sample container 506 includes a water chamber 575, which may be loaded with a predetermined quantity of water, for receiving the water chamber piston 510. The water chamber piston 510, which may have a piercing tip configured to pierce a seal on the sealed PCR sample tube, is dimensioned to be inserted through the water chamber 575 and extend at least partially through the seal on the PCR sample tube to create an opening in the seal to permit water from the water chamber 575 to enter the PCR sample tube 507 to contact/rehydrate a dried/lyophilized master mix 517 contained therein.

The sample container 506 also includes a saliva piston metering channel 560 for receiving the metering piston 508. The saliva piston metering channel 560 is in fluid communication with the micro sample chamber 516 and also may be in fluid communication with the bulk saliva collection chamber 514. The metering piston 508 may have a piercing tip configured to pierce a seal on the sealed PCR sample tube 507. The metering piston 508 is dimensioned to be inserted through the saliva piston metering channel 560 and extended at least partially through the seal on the PCR sample tube to create an opening in the seal to permit the selected volume of the saliva from the micro sample chamber 516 to enter the PCR sample tube 507.

Figure 5F:
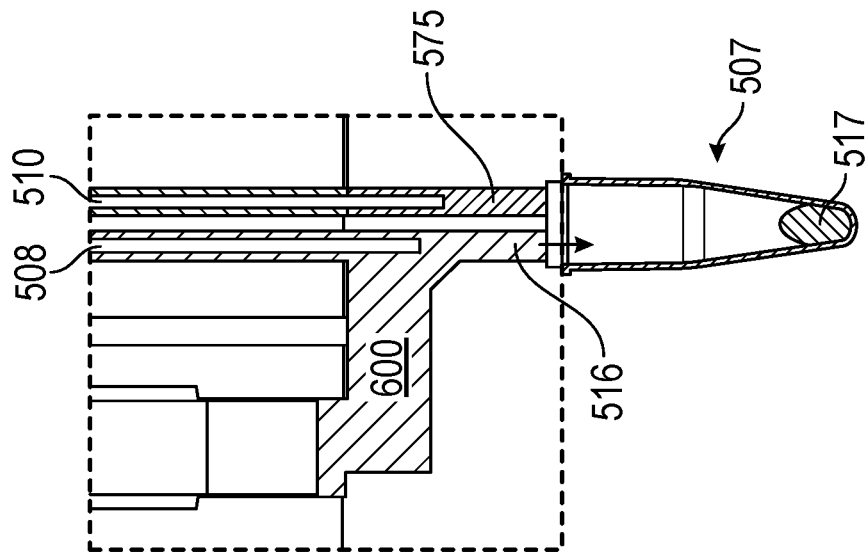
FIGS. 5E-5F are close-up cross-sectional views of a portion of an example SCD, illustrating operations therein when the plunger is pressed, according to one embodiment of the present disclosure.
Figure 5E:
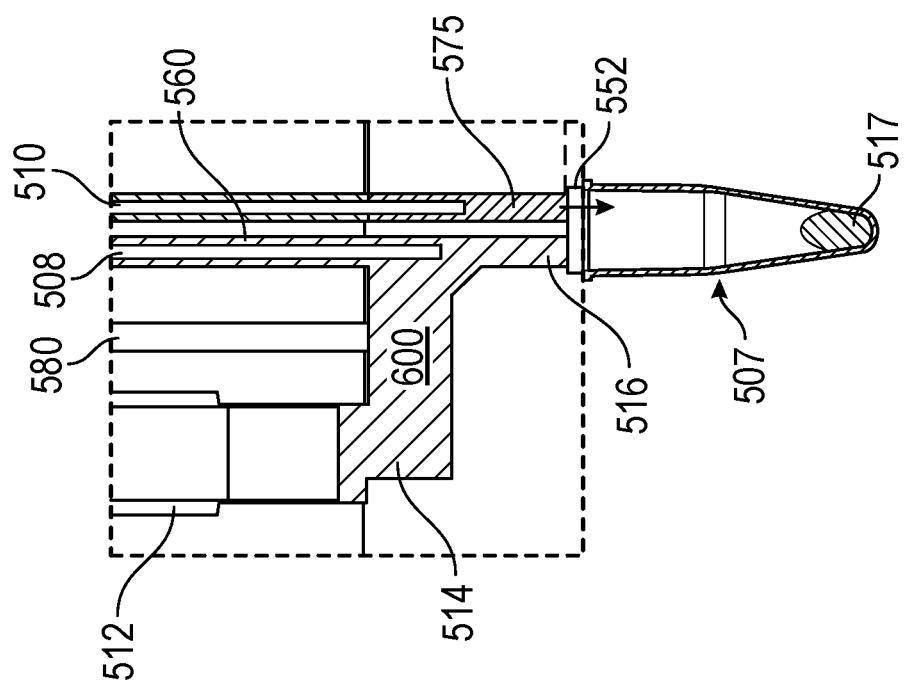

In use, fluid flow within the sample container 506 may be more clearly understood with reference to FIGS. 5E-5F. After collection of a saliva specimen, the absorbent swab 504, containing the saliva specimen, is inserted into swab chamber 512. Then, the SCD 500 is inserted into a testing module, which may carry out the following operations. The absorbent swab 504 is compressed to release the saliva specimen (similarly to the operation of the swab and sample container in SCD 300 described above) into the bulk saliva collection chamber 514. Simultaneously, air displaced by the saliva entering the bulk saliva collection chamber 514 may escape through the air vent 580 to equalize the pressure within the bulk saliva collection chamber 514.

Subsequently, the saliva in the bulk saliva collection chamber 514 is lysed. In an embodiment, the saliva is thermally lysed. In some embodiments, the saliva or other sample may be lysed using chemical reagents known in the art. In some embodiments, the chemical lysing agents may be pre-loaded in the SCD. The lysing may include a combination of chemical and thermal lysing.

Saliva is permitted to flow from the bulk saliva collection chamber 514 into the micro sample chamber 516. This may occur before or after lysing, depending on the position of the metering piston 508, which may control flow of the saliva from the bulk saliva collection chamber 514 into the micro sample chamber 516, as well as into the PCR sample tube 507. Specifically, when the metering piston 508 is inserted into the micro sample chamber 516, it may block flow of saliva from flowing from the bulk saliva collection chamber 514 into the micro sample chamber 516. When the metering piston 508 is in a retracted configuration, such as illustrated in FIGS. 5E-5F, or located out of the saliva piston metering channel 560, then saliva is able to flow from the bulk saliva collection chamber 514 into the micro sample chamber 516.

At the appropriate time for rehydration of the master mix 517 in PCR sample tube 507, the water chamber piston 510 is inserted through the water chamber 575 and pierces the seal 552, covering the PCR sample tube 507, causing water located in the water chamber 575 to enter the PCR sample tube 507, as indicated by the arrow in FIG. 5F, to contact/rehydrate the master mix 517 contained therein.

Before, contemporaneously, or after the water is added to the PCR sample tube 507, the metering piston 508 is inserted through the saliva piston metering channel 560 and pierces the seal 552 on the PCR sample tube, causing the selected volume, e.g., 5 μl, of the lysed saliva to flow from the micro sample chamber 516 into the PCR sample tube 507, as indicated by the arrow in FIG. 5E.

Once the PCR sample tube 507 contains the water, master mix 517, and the selected volume of the lysed saliva, the testing module then applies ultrasonic energy to mix together the components in the PCR sample tube. The testing module then separates the SCD from the PCR sample tube and then seals the sample tube, e.g., with a film or foil material known in the art. The testing module then may place the PCR sample tube in a PCR machine and run a PCR test on the same in the PCR sample tube. The testing module may discard the used SCD into a waste receptacle. Once the PCR test is complete, then the testing module may also discard the sample tube into a waste receptacle.

Figure 6:
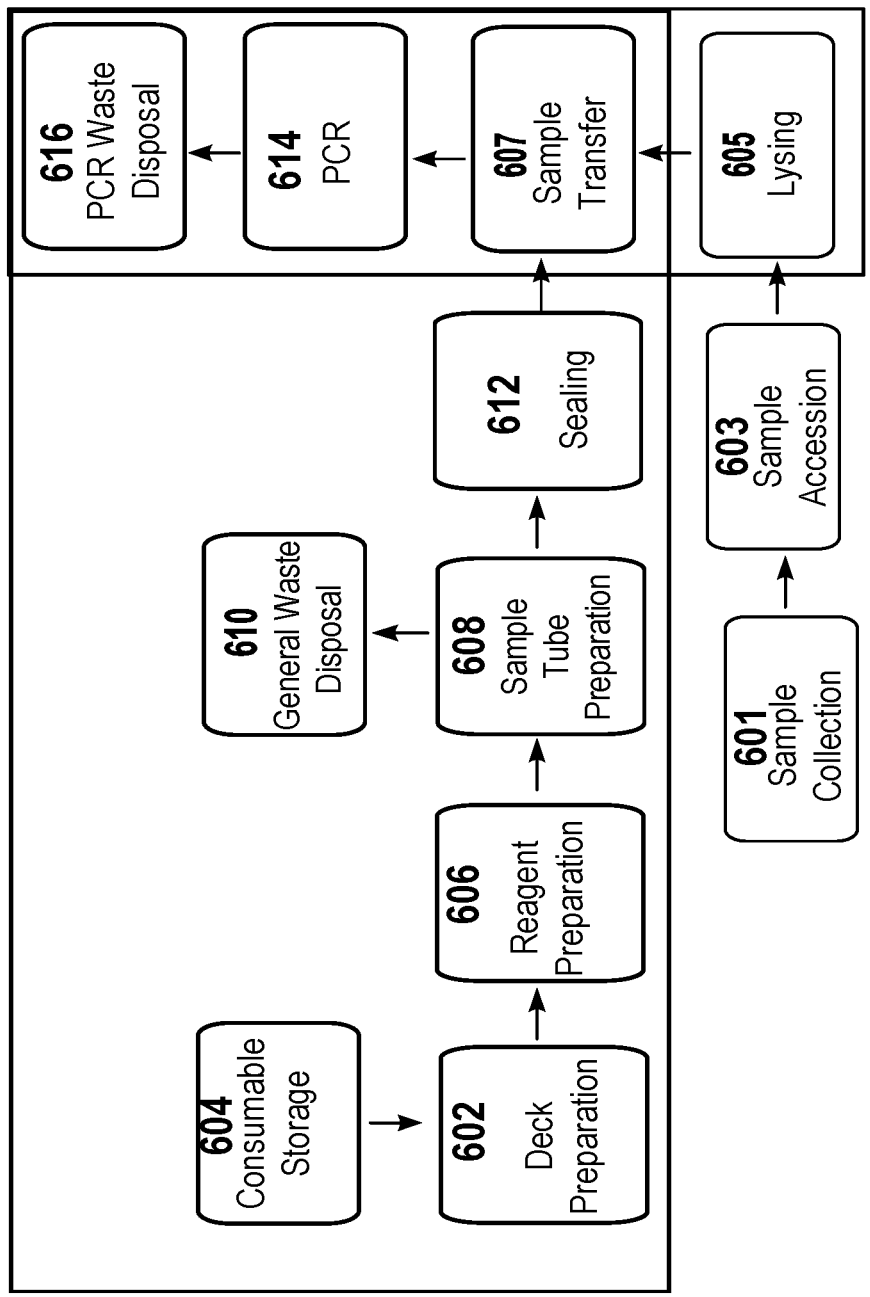
FIG. 6 is an example process flow diagram for rapid PCR testing, according to one embodiment of the present disclosure.

FIG. 6 is an example process flow for rapid PCR testing within a testing module, useful with the presently disclosed sample collection devices. The testing module may include various components for processing the collected sample within the SCD and within the PCR sample tube. The testing module may include a barcode scanner, one or more robot arms with actuators, reagents, storage for reagents and consumables, reagent plates, water, dispensers, pipette heads, PCR tubes and/or plates, waste receptacles, a sealer, and one or more PCR machines. Lysing and inactivation of the sample may be performed by the testing module or separately before the SCD and sample are placed into the testing module. The testing module may scan the sample, prepare reagents and mix them with the sample, prepare and seal a PCR tube, and run it through a PCR machine. The testing module also collects and disposes of the waste used in each step.

As shown in FIG. 6, the testing module may perform various steps to prepare for receipt of the sample. Examples of these steps include deck preparation step 602, consumable storage step 604, reagent preparation step 606, PCR sample tube preparation step 608, general waste disposal step 610, and sealing step 612. Once the sample is received by the testing module, the testing module performs lysing step 605, sample transfer step 607, in which the sample is transferred into the sample tube, PCR testing step 614, and PCR waste disposal step 616. To prepare for receipt of the sample, the testing module first prepares the deck within the testing module at deck preparation step 602. The testing module may prepare the deck with the assistance of a robot arm with an actuator. At consumable storage step 604, the testing module may remove consumables, including reagents, from a storage rack. The testing module may then prepare the reagents at reagent preparation step 606. Reagent preparation step 606 may include use of a reagent plate, dispenser, pipette, and pipette heads. For example, the testing module may mix various reagents together, such as water, polymerase, primers, and/or buffer. At PCR sample tube preparation step 608, the PCR sample tube is prepared. If a PCR plate is used, then a standard-sized plate, for example, a 6, 8, 12, 24, 48, or 96-well plate, may be used. The testing module optionally disposes of waste at general waste disposal step 610. Waste disposed at general waste disposal step 610 may include used pipette tips and reagent plates or PCR sample tubes, and used SCDs. At sealing step 612, the PCR sample tube is sealed, for example using a film or closure (e.g., cap or plug).

The sample is collected by the user using a SCD at sample collection step 601. At sample accession step 603, the sample is subjected to an accessioning process. In FIG. 6, sample accessioning takes place outside the testing module; however, in embodiments sample accessioning may be performed by the testing module instead. Sample accession step 603 may include scanning the SCD and/or the PCR sample tube, associating the sample with a specific patient/user, and/or a quality control check of the sample. The sample is then placed in the testing module. At lysing step 605, the testing module lyses the sample in the SCD. The testing module may also inactivate the sample during lysing step 605. At PCR step 614, the testing module adds the lysed sample to the prepared PCR sample tube and performs a PCR test on the sample. At PCR waste disposal step 616, the testing module optionally disposes of any PCR waste, such as the used PCR sample tube and tested biological sample.

Figure 7:
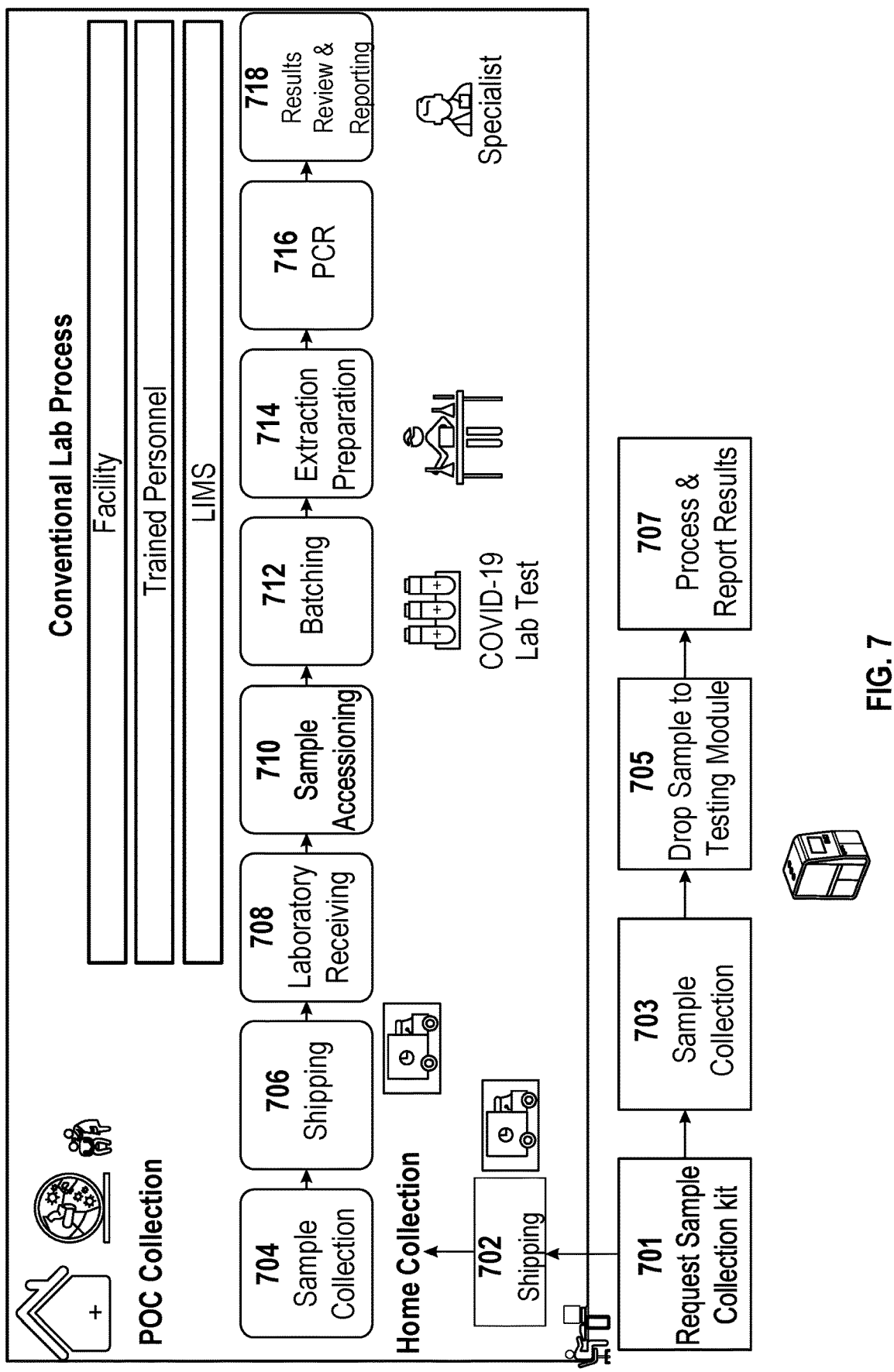
FIG. 7 depicts an example process flow of a conventional lab process of PCR testing as contrasted with a rapid method of PCR testing according to one embodiment of the present disclosure.

FIG. 7 illustrates the time-consuming steps involved in conventional lab processes of PCR testing as compared to the fewer and more rapid steps possible with the method of PCR testing described herein. The conventional lab process may include either a home collection process or a point-of-care collection process done at a mobile or brick-and-mortar healthcare facility. For home collection, a user must first request a sample collection kit at Step 701. The sample collection kit is then shipped to the user at Step 702. The user collects the sample using the shipped sample collection kit at Step 704. Alternatively, if point-of-care collection is being used, then either the user or a healthcare professional may collect the sample at the point-of-care site at Step 704. The collected sample is then shipped to a laboratory at Step 706. At Step 708, the laboratory receives the sample. At Step 710, the sample undergoes a sample accessioning process. The sample accessioning process may include labeling, sorting, receipt, and recordation of data about the sample and/or a quality control check of the sample. At step 712, the sample is batched with other samples. At Step 714, the sample is prepared for extraction. At Step 716, a PCR test is performed on the sample, and results are generated. At Step 718, a specialist reviews the results of the PCR test and reports those results. Conversely, the method of PCR testing described herein includes fewer steps and is faster when compared with conventional lab processes of PCR testing. Using the methods described herein, the user first obtains a sample collection kit at Step 701. This may occur at the location where the testing module is located (e.g., a pharmacy, a mobile or brick-and-mortar health care facility, an office building, a public transportation center, such as an airport or train station, etc.). At Step 703, the user uses the sample collection kit (i.e., an SCD) to collect the sample, and then the sample is placed into the testing module at Step 705, for example, directly by the user or indirectly by another, for example, a healthcare professional. At Step 707, the testing module processes the sample and reports the results to the user.

Figure 8:
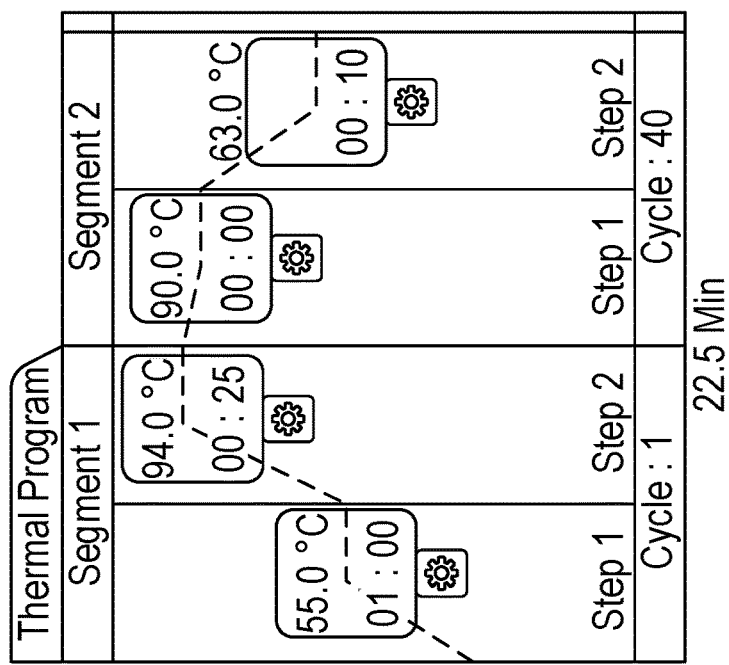
FIG. 8 shows two graphs that illustrate a conventional PCR profile (on left) and a PCR profile according to one example of a PCR profile with the methods and devices described herein (on right).
Figure 8:
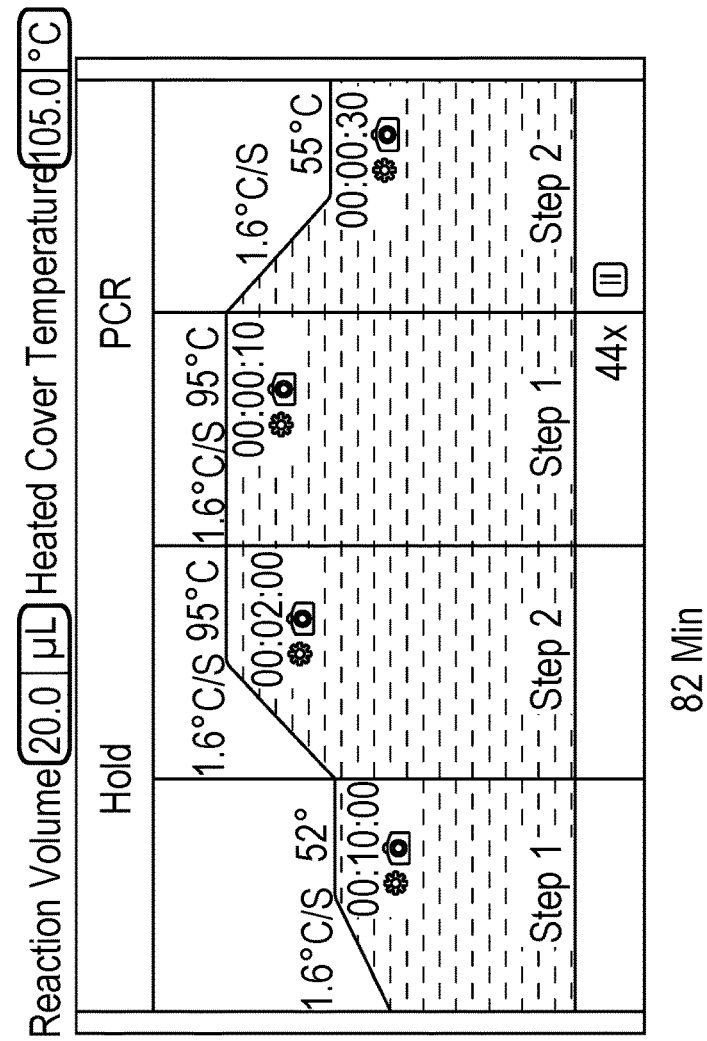

The presently disclosed SCDs and the local testing modules advantageously may eliminate the need for shipping samples and may yield a faster the PCR profile as compared with PCR profiles provided with conventional testing methods. As shown in FIG. 8, both conventional PCR machines and the testing module perform one or more thermal cycles during PCR testing. Such thermal cycles include raising and lowering the temperature of the sample to assist with the annealing and amplification process, as known in the art. In the illustrated conventional process, the process includes increasing the sample temperature from ambient to 52° C. at 1.6° C./sec, holding for 10 minutes, increasing to 95° C. at 1.6° C./sec, holding at 95° C., and cooling to 55° C. at 1.6° C./sec, with 44 cycles, taking a total of 82 minutes to produce the results. However, the process using the testing module described herein, in the illustrated embodiment, may include increasing the sample temperature from ambient to 55° C., holding, increasing to 94° C., holding, decreasing to 90° C., and cooling to 63° C., with 40 cycles, taking a total of less than 23 minutes to produce the results. In some embodiments, the rates of heating and cooling of the samples in the PCR machine of the testing modules described herein may range from 0.5° C./second to 5.0° C./second. In embodiments, the testing module may subject the sample to fewer thermal cycles than a conventional PCR machine. Table 1 below shows various methods of current methods of COVID-19 testing, which are slower and/or provide low throughput.

TABLE 1

| Test Assay | Average TAT | Test W/EUA | Throughput |
|---|---|---|---|
| RT-PCR | >60 minutes | BGI Covid-19, TaqPath COVID-19 combo kit | High throughput |

TABLE 1-continued

| Test Assay | Average TAT | Test W/EUA | Throughput |
|---|---|---|---|
| RT-PCR (Cartridge or Self Contained Reagent) | ~45 minutes | BioFire Covid-19 test, Xpert Xpress SARS-CoV-2 test | 1 sample per run |
| RT-Lamp (Isothermal) | 30-45 minutes | ID NOW COVID-19, iAMP COVID-19 detection kit | 1 sample per run |
| Micro-Fluidics RT-PCR | 20-40 minutes | VITAPCR SARS-CoV-2 assay | 1 sample per run |
| RT-PCT + Lateral Flow | ~30 minutes | Accula SARS-CoV-2 test | 1 sample per run |

While the test modules, SCDs, and methods herein are particularly useful in analyzing clinical specimens for the presence of infectious agents, such as those associated with various viruses, including the SARS-CoV-2 virus and influenza, the SCDs and methods described herein also can be used or readily adapted for use in the screening or diagnosis of a variety of other diseases and conditions in which PCR testing may be utilized. Non-limiting examples include measles, mumps, chlamydia, *Bordetella pertussis* Toxin, tuberculosis, *H. pylori*, zika, *Mycoplasma pneumoniae*, varicella zoster virus, VAV, borrelia, chagas, and sepsis. In other examples, the methods and devices described herein may be used in the screening of various other medical conditions, such as those related to bone and mineral health, thyroid, reproductive endocrinology, anemia, autoimmunity, tumor markers, hypertension, adrenal function, growth, diabetes, viral hepatitis and retroviruses, treponema, Epstein-Barr Virus, TORCH (toxoplasmosis, rubella cytomegalovirus, herpes simplex, and HIV), as well as in stool diagnostics. PCR assays are known in the art for use in the diagnosis of a wide variety of diseases.

Figure 9:
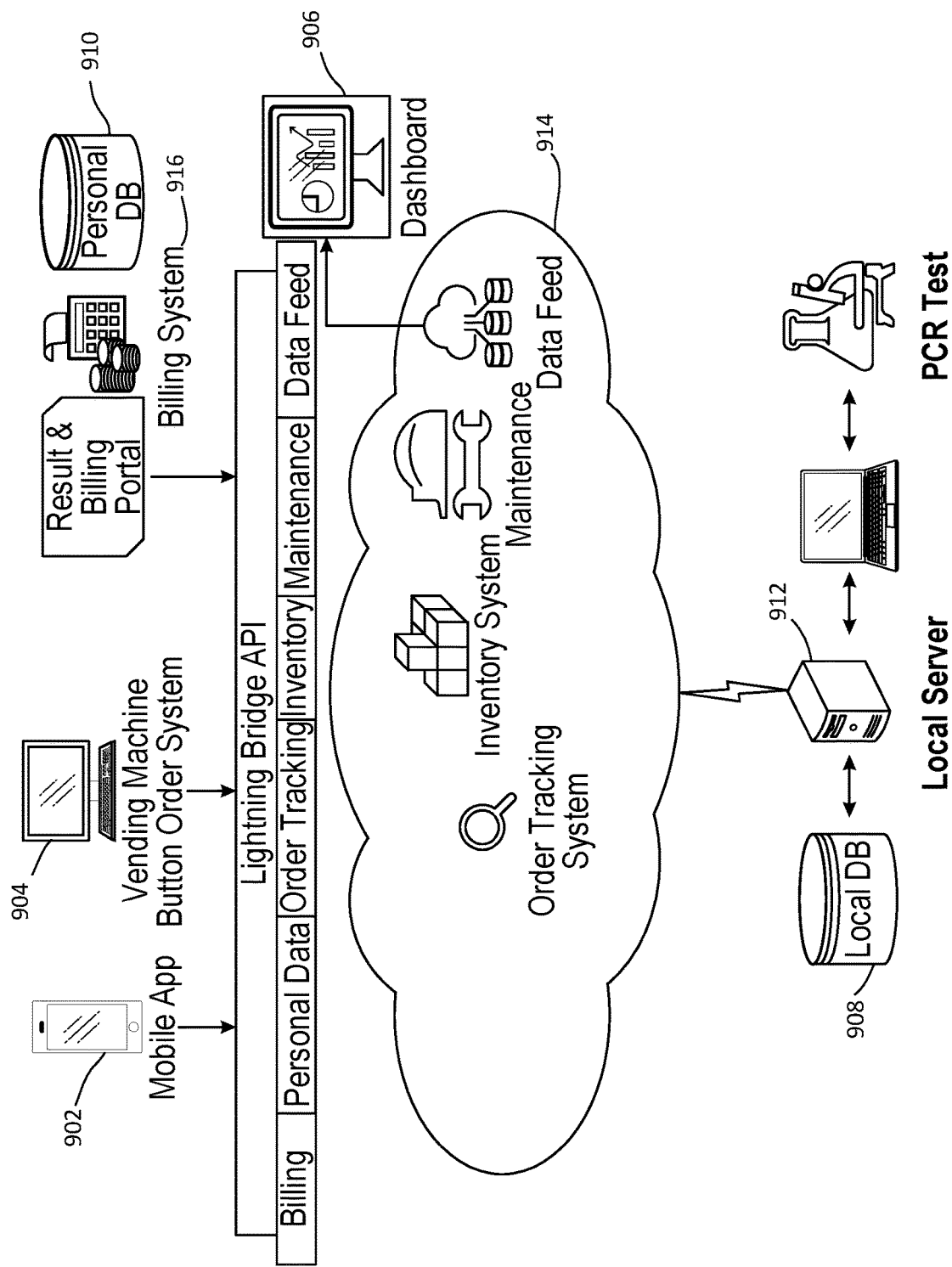
FIG. 9 is an example process flow of software systems supporting the diagnostic sample collection and test module systems according to one embodiment of the present disclosure.

FIG. 9 illustrates one example of information flow in a hardware and software system supporting the rapid PCR testing system and methods described herein. For example, the system will enable a patient to order a test online using a mobile device 902 (or any other suitable computing device, such as a tablet or computer) or (while present at) a local PCR testing module 912. Computing devices may be in operable communication with the testing module. For example, a phone, tablet, or other mobile device 902 may be configured to communicate with a controller to provide instructions and/or receive feedback from the software system via one or more networks. The testing module 912 may be configured to operate like a "vending machine" with buttons (e.g., a keypad) for a user to interface with the testing module 912, as a vending machine button order system 904. The system may include a billing system 916 with a result and billing portal. A B2B dashboard 906 may be provided to enable effective management of the test module 912 and related systems, providing maintenance indicators, as well as inventory and replenishment indicators that are user configurable. The testing module software manages end-to-end sample handling and result generation. Data may be stored in a local database 908 and/or a personal database 910; however, the testing module 912 itself is not in possession of patient data. All direct interaction is serviced from the cloud 914. The cloud 914 may include an order tracking system, an inventory system, a maintenance system, and a data feed system. The local database 908 and personal database 910 may comprise memory for storing data, such as test results and/or computer-executable instructions. When running in offline mode, the testing module only handles and reports sample barcode results. In embodiments, PCR test results may be sent to a dashboard 906 or mobile device 902.

Figure 10:
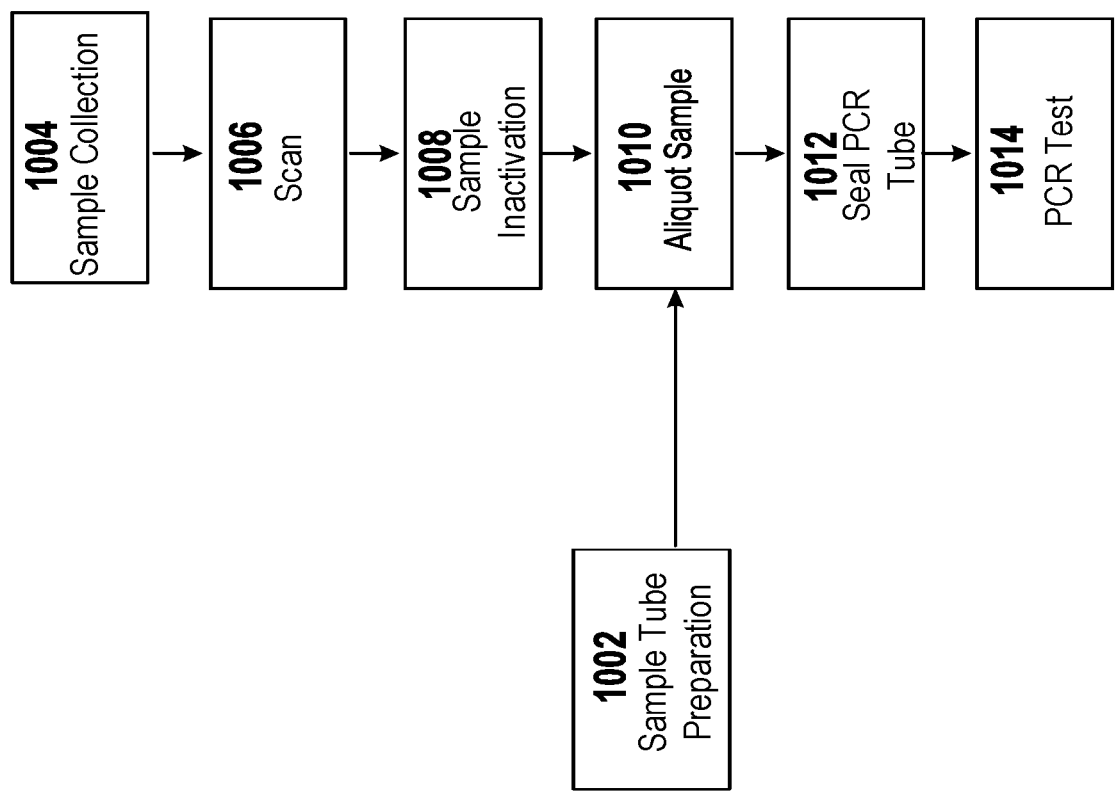
FIG. 10 is an example process flow for processing of a sample in a testing module, according one embodiment of the present disclosure.

FIG. 10 depicts an example process flow for processing a sample in a testing module. First, before a sample may be processed, a PCR sample tube is prepared at Step 1002. The PCR tube may be prefilled with lyophilized reagents, which are then rehydrated. In embodiments, liquid reagents are mixed in the PCR tube. The reagents may include water, polymerase, primers, and/or buffer. The PCR tube may be a single tube allowing a sample to be tested individually; however, a PCR plate may be used. The PCR plate may have a standard number of wells, such as 6, 8, 12, 24, 48, or 96 wells. In embodiments, the PCR tube is prepared outside the testing module and then placed in the testing module. In embodiments, the testing module prepares the PCR tube.

The biological sample is collected with an SCD at step 1004. For example, the SCD may include either a nasal or oral swab for collection of the sample, and the SCD may comprise water and/or reagents to be mixed with the sample. In embodiments, the SCD has a barcode or QR code, or other means of identifying/tracking the SCD. Once the sample is collected, the SCD is placed in the testing module. At step 1006, the testing module scans the SCD so that a sample may be associated with a particular user or patient.

Once the sample has been identified, the sample may be inactivated at Step 1008. In some embodiments, the sample may be heated to render the sample non-infectious, for example, to 95° C. for an effective period of time as known in the art. In some other embodiments, the sample may be irradiated, filtered, or exposed to solvents, detergents, or reagents with a low pH, as known in the art. The sample is also lysed, using techniques known in the art. Lysing may include exposing the sample to a detergent. In embodiments, the sample may be inactivated and lysed simultaneously. In some embodiments, the sample may be inactivated and lysed via heat; in such embodiments, the testing module comprises an oven or heaters known in the art.

In one embodiment, after the sample is lysed and inactivated, it may be added to a PCR tube at Step 1010. While the testing module can be used to test a single sample, it may also be used to test numerous samples at a time. In embodiments, the testing module comprises PCR plates with multiple wells. In embodiments, the testing module comprises more than one PCR tube and/or plate. The testing module comprises a liquid handler for filling the PCR tubes. In embodiments, consumable pipette tips are used to fill the tubes and are disposed of by the testing module. The sample is removed from the test tube before being added to a PCR tube. The liquid added to the PCR tube has a small volume, such as 5 uL. Once the sample has been removed from the test tube, the test tube is also disposed of by the testing module.

PCR sample tubes are sealed in step 1012. In some embodiments comprising a PCR plate, the testing module waits to test samples until a PCR plate is full. In some embodiments, the samples may be tested when the PCR plate is partially full. After the PCR plate is filled with the number of samples to be tested, it is sealed. Accordingly, the testing module may include a sealer for sealing the PCR plate, including consumables such as seal film, which are known in the art. In some embodiments comprising PCR sample tubes, the testing module may continuously run PCR tests, with sample tubes being continually added to and removed from the PCR machine. In those cases, the PCR tubes are sealed individually following receipt of a sample. Accordingly, the testing module may include a sealer for sealing the PCR sample tubes, including consumables such as seal film or closures (e.g., caps, plugs), which are known in the art.

At step 1014, PCR tests are performed on the sealed samples, and results of the PCR test are generated and reported as appropriate. Once the PCR testing is complete, the PCR tubes or plate are discarded, for example, into a waste bin in the testing module.

The testing module itself may include one or more robotic manipulators (e.g., arms with actuators) reagents, storage for reagents and consumables, reagent plates, water, dispensers, pipette heads, PCR tubes and/or plates, waste receptacles, a tube/plate sealer, and one or more PCR machines. The testing module may scan the sample, prepare reagents and mix them with the sample, prepare and seal a PCR tube, and run it through a PCR machine.

Figure 11:
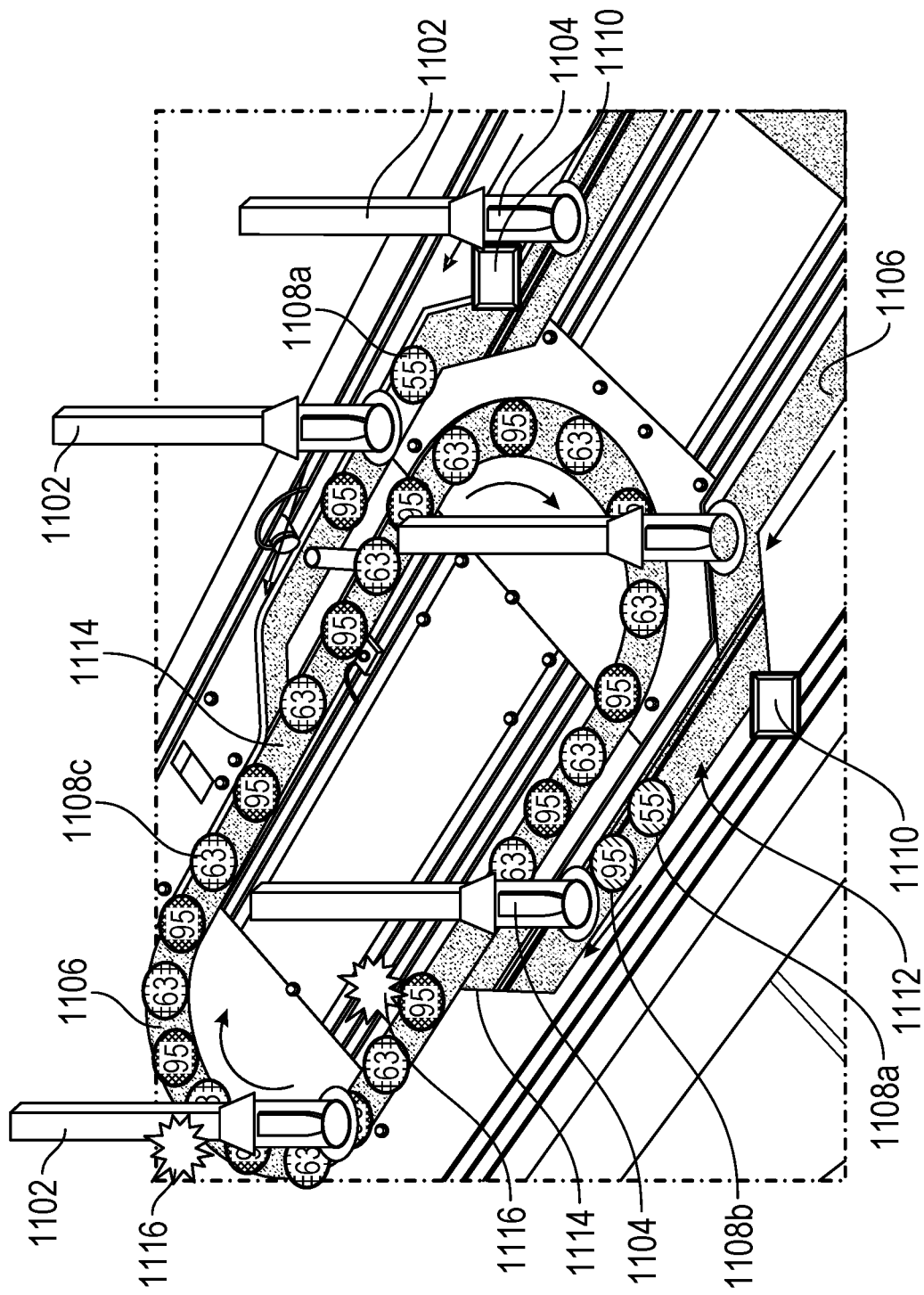
FIG. 11 is an example rotary PCR process, according to one embodiment of the present disclosure.
Figure 12:
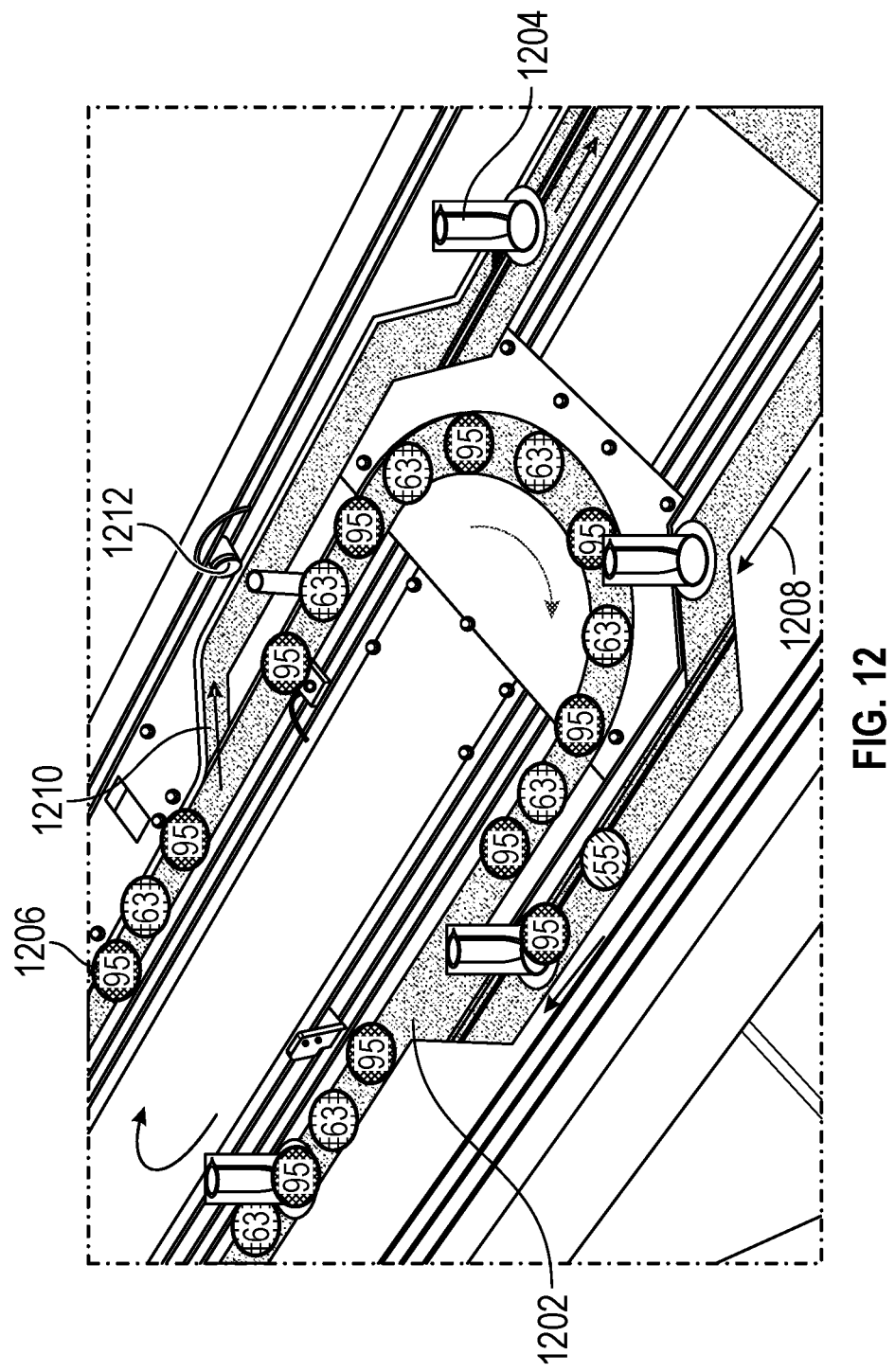
FIG. 12 is an example rotary PCR process, according to one embodiment of the present disclosure.
Figure 13:
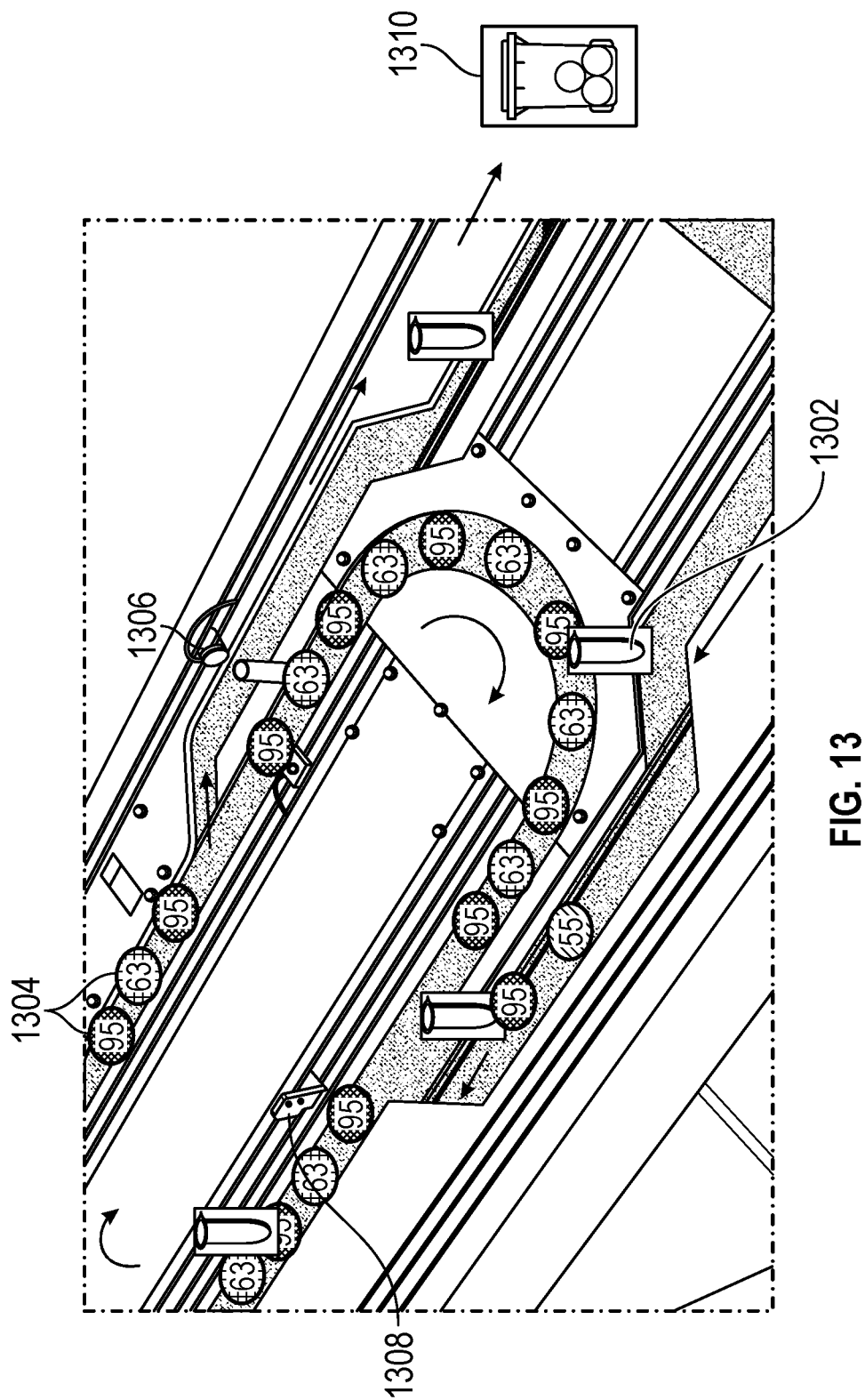
FIG. 13 is an example rotary PCR process, according to one embodiment of the present disclosure.

In some embodiments, the PCR machine comprises a continuous PCR system, which is sometimes referred to as a rotary PCR system, as depicted in FIGS. 11-13. The PCR system includes a sample scanner configured to read a bar code on the PCR sample tube; a conveyor system for moving a plurality of received PCR sample tubes through heating and cooling zones within the PCR machine; and an array of laser diodes and photodetectors to detect the fluorescent intensity in the PCR sample tube as the PCR sample tube is conveyed through thermal cycles. The conveyor system is configured to eject the PCR sample tube into the biohazard bin upon completion of testing.

The conveyor system may include vacuum grippers (or suction cup holders, or vacuum end effectors) and a track as known in the art. Vacuum grippers 1102 move the PCR sample tubes 1104 through a rotary PCR process. The vacuum grippers 1102 may move along a track 1106. The track may include stationary thermal holders 1108a, 1108b, 1108c. The stationary thermal holders 1108a, 1108b, 1108c may have different temperatures to assist with exposing the sample tubes to thermal cycles in the PCR process, effectively creating heating and cooling zones with the PCR system. In some embodiments, the stationary thermal holders 1108a, 1108b, 1108c are configured to heat the sample tubes 1104 to 55° C., 63° C., and 95° C., respectively. The vacuum grippers 1102 convey the sample tubes 1104 along the track 1106 from one thermal holder 1108a, 1108b, 1108c to the next thermal holder 1108a, 1108b, 1108c. In FIG. 11, the direction of movement follows the arrows.

Before beginning a PCR test on a sample tube 1104, it is scanned with a sample scanner 1110 in order to identify the specific sample carried by each respective sample tube 1104. Then, the samples go through the reverse transcription stage 1112 before being moved to the oval portion of the track 1106. The oval portion of the track 1106 may have more than one entry point 1114 to increase efficiency of the testing module. For example, the rotary PCR system depicted in FIG. 11 has two entry points 1114, such that the testing module can perform two sets of the reverse transcription stage 1112 simultaneously. The reverse transcription stage 1112 may comprise moving the sample tubes 1104 to a first thermal holder 1108a at 55° C. and then to a second thermal holder 1108b at 95° C. The vacuum grippers 1102 move the sample tubes 1106 along the oval portion of the track 1106 for the PCR cycles. In embodiments, the sample tubes 1106 are subjected to alternating temperatures of 95° C. and 63° C. for 40 cycles.

Each thermal holder 1108a, 1108b, 1108c, may be equipped with a photodetector 1116 and a light source (e.g., laser diodes). As a sample tube 1104 moves through the rotary PCR process, it may be subjected to a photodetector 1116 at each thermal holder 1108a, 1108b, 1108c. As the sample tube 1104 moves along the PCR rotary system, if the sample comprises the virus of interest, that virus is amplified. Once the viral signals within each sample reach a high enough level, a photodetector 1116 can detect fluorescence within the sample tube 1104. If the fluorescence is detected, then the testing module generates a positive test result, which the test module can report to the patient. After fluorescent detection, the vacuum gripper 1102 moves the sample tube 1104 to a biohazard bin. Alternatively, if no fluorescence is detected the vacuum grippers 1102 moves the sample tube 1104 to the next thermal holder 1108c, at which point the sample is again subjected to a photodetector 1116. After the PCR cycles, if no fluorescence is detected in the sample, then the vacuum gripper 1102 moves the sample tube 1104 to a biohazard bin, and the testing module generates a positive test result, which the test module can report to the patient.

FIG. 12 illustrates an example of how a conveyor belt 1202 may move PCR sample tubes 1204 from one stationary thermal holder 1206 to another stationary thermal holder 1206. The samples 1204 enter the PCR system at the entry point 1208, where they are scanned and subjected to a reverse transcription process. The sample tubes 1204 may then enter the oval portion of the conveyor belt 1202, which transports the sample tubes 1204 between thermal holders 1206 at alternating temperatures. In embodiments, the temperatures are 95° C. and 63° C. The sample tubes 1206 are circulated about the oval portion of the convey belt 1202 until they have reached the desired number of cycles through the PCR testing process. The sample tubes 1204 may be transferred along the oval portion of the conveyor belt 1202 once or more than once. In embodiments, the sample tubes 1204 are transported around the oval portion of the convey belt 1202 four rounds and are subjected to 10 cycles each round; in such embodiments, the sample tubes 1204 go through 40 cycles in the PCR testing process. At the end of the PCR process, the sample tubes 1204 are directed to an exit point 1210 and then are examined by a photodetector 1212. If the photodetector 1212 detects a signal, the testing module will identify the sample in the sample tube 1204 as positive for the agent to be detected and report a positive result. Both positive and negative sample tubes 1204 are then transported to the end of the conveyor belt 1202 and deposited in a biohazard bin.

FIG. 13 depicts an example continuous PCR system. The sample, reagents, and water are contained within a PCR sample tube 1302 prior to entering the PCR system. A vacuum gripper picks up a seal cover and applies it over the PCR sample tube 1302. The PCR sample tube 1302 is then lifted by the vacuum gripper and queued to enter the PCR system, where it is scanned by a scanner 1308 near the entrance.

The PCR sample tube 1302 conveyed through the PCR system, going through heating and cooling cycles at various thermal stations 1304. An array of laser diodes and photodetectors 1306 are staggered through the PCR system path to detect fluorescent intensity as the PCR sample tube 1302 moves through the thermal cycles. At least one photodetector 1306 is located at the exit of the PCR process. As soon as a photodetector 1306 identifies a sample as positive, the PCR sample tube 1302 is conveyed to a biohazard bin 1310, and the test results are sent to the cloud. The photodetector 1306 at the exit of the PCR process serves to confirm the results. After a certain number of cycles, for example, 40, if a sample has not been identified as positive, then it is identified as negative, and the test results are sent to the cloud. The PCR sample tube 1302 is then conveyed to a biohazard bin 1310.

Illustrative Computer Architecture

Figure 14:
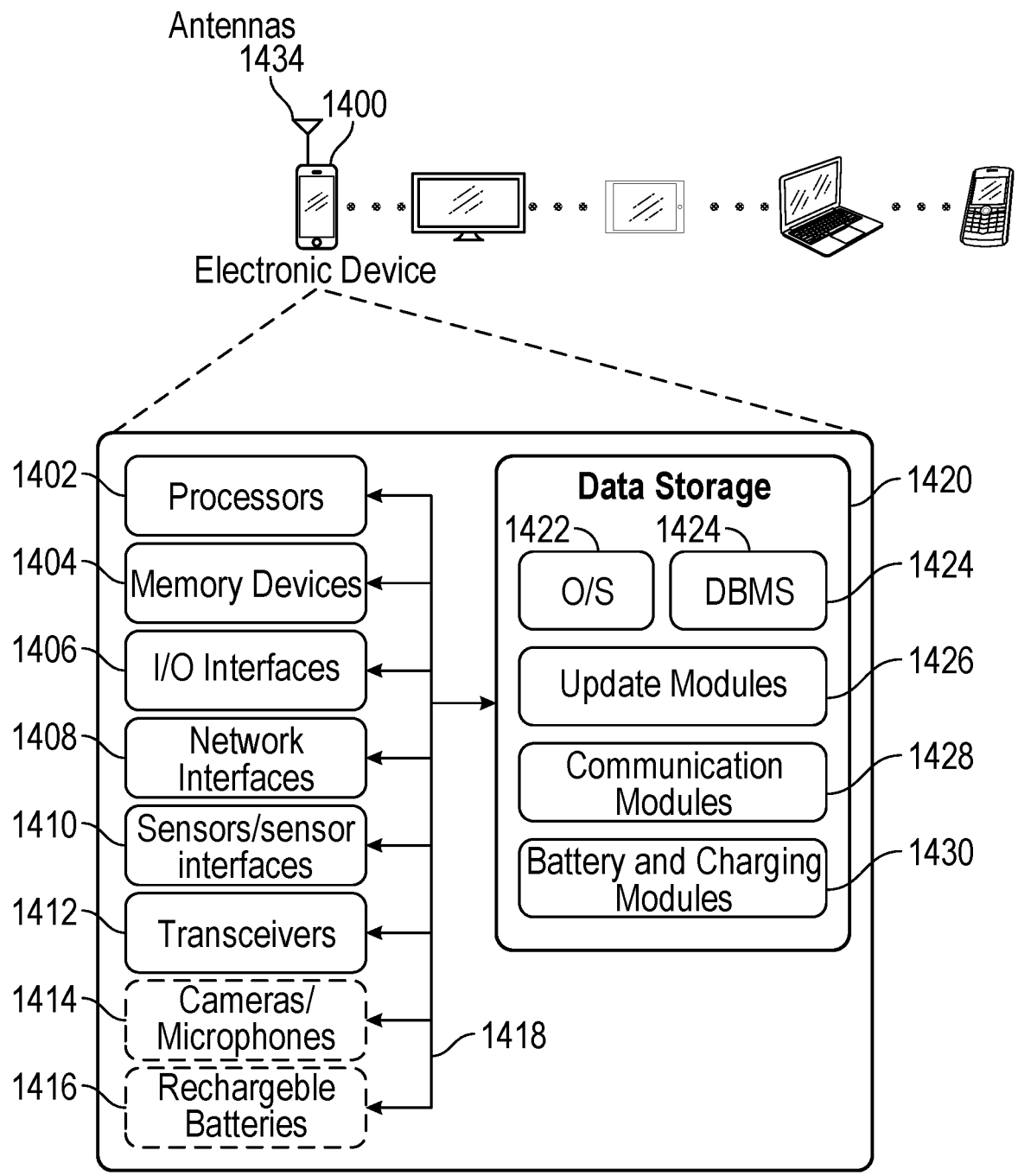
FIG. 14 schematically illustrates an example architecture of an electronic device in accordance with one or more embodiments of the disclosure.

FIG. 14 is a schematic block diagram of one or more illustrative electronic device(s) 1400 in accordance with one or more example embodiments of the disclosure. The electronic device(s) 1400 may control the rapid PCR diagnostic system disclosed herein. The electronic device(s) 1400 may include any suitable computing device including, but not limited to, a server system, a mobile device such as a smartphone, a tablet, an e-reader, a wearable device, or the like; a desktop computer; a laptop computer; a content streaming device; a set-top box; a scanning device; or the like.

The electronic device(s) 1400 may be configured to communicate with one or more servers, user devices, or the like. The electronic device(s) 1400 may be any suitable device, such as a mobile device, and may optionally be configured to determine voice commands, determine wake-word utterances, determine and/or control other devices, and other operations. The electronic device(s) 1400 may be configured to present content, detect sound, output digital content, and other functionality In some embodiments, a single remote server or a single group of remote servers may be configured to perform more than one type of functionality in conjunction with an electronic device.

The electronic device(s) 1400 may be configured to communicate via one or more networks. Such network(s) may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. Further, such network(s) may have any suitable communication range associated therewith and may include, for example, global networks (e.g., the Internet), metropolitan area networks (MANs), wide area networks (WANs), local area networks (LANs), or personal area networks (PANs). In addition, such network(s) may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In an illustrative configuration, the electronic device(s) 1400 may include one or more processors (processor(s)) 1402, one or more memory devices 1404 (also referred to herein as memory 1404), one or more input/output (I/O) interface(s) 1406, one or more network interface(s) 1408, one or more sensor(s) or sensor interface(s) 1410, one or more transceiver(s) 1412, one or more optional camera(s) and/or microphone(s) 1414, one or more optional rechargeable batteries 1416, and data storage 1420. The electronic device(s) 1400 may further include one or more bus(es) 1418 that functionally couple various components of the electronic device(s) 1400. The electronic device(s) 1400 may further include one or more antenna(s) 1434 that may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals, a Near Field Communication (NFC) antenna for transmitting or receiving NFC signals, and so forth. These various components will be described in more detail hereinafter.

The bus(es) 1418 may include at least one of a system bus, a memory bus, an address bus, or a message bus, and may permit the exchange of information (e.g., data (including computer-executable code), signaling, etc.) between various components of the electronic device(s) 600. The bus(es) 1418 may include, without limitation, a memory bus or a memory controller, a peripheral bus, an accelerated graphics port, and so forth. The bus(es) 1418 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnect (PCI) architecture, a PCI-Express architecture, a Personal Computer Memory Card International Association (PCMCIA) architecture, a Universal Serial Bus (USB) architecture, and so forth.

The memory 1404 of the electronic device(s) 1400 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 1404 may include multiple different types of memory, such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 1404 may include main memory as well as various forms of cache memory such as instruction cache(s), data cache(s), translation lookaside buffer(s) (TLBs), and so forth. Further, cache memory, such as a data cache, may be a multi-level cache organized as a hierarchy of one or more cache levels (L1, L2, etc.).

The data storage 1420 may include removable storage and/or non-removable storage, including, but not limited to, magnetic storage, optical disk storage, and/or tape storage. The data storage 1420 may provide non-volatile storage of computer-executable instructions and other data. The memory 1404 and the data storage 1420, removable and/or non-removable, are examples of computer-readable storage media (CRSM) as that term is used herein.

The data storage 1420 may store computer-executable code, instructions, or the like that may be loadable into the memory 604 and executable by the processor(s) 1402 to cause the processor(s) 1402 to perform or initiate various operations. The data storage 1420 may additionally store data that may be copied to the memory 1404 for use by the processor(s) 1402 during the execution of the computer-executable instructions. Moreover, output data generated as a result of execution of the computer-executable instructions by the processor(s) 1402 may be stored initially in the memory 1404, and may ultimately be copied to the data storage 1420 for non-volatile storage.

More specifically, the data storage 1420 may store one or more operating systems (O/S) 1422; one or more database management systems (DBMS) 1424; and one or more program module(s), applications, engines, computer-executable code, scripts, or the like such as, for example, one or more update module(s) 1426, one or more communication module(s) 1428, and/or one or more battery and charging module(s) 1430. Some or all of these module(s) may be sub-module(s). Any of the components depicted as being stored in the data storage 1420 may include any combination of software, firmware, and/or hardware. The software and/or firmware may include computer-executable code, instructions, or the like that may be loaded into the memory 1404 for execution by one or more of the processor(s) 1402. Any of the components depicted as being stored in the data storage 1420 may support functionality described in reference to corresponding components named earlier in this disclosure.

The data storage 1420 may further store various types of data utilized by the components of the electronic device(s) 1400. Any data stored in the data storage 1420 may be loaded into the memory 1404 for use by the processor(s) 1402 in executing computer-executable code. In addition, any data depicted as being stored in the data storage 1420 may potentially be stored in one or more datastore(s) and may be accessed via the DBMS 624 and loaded in the memory 1404 for use by the processor(s) 1402 in executing computer-executable code. The datastore(s) may include, but are not limited to, databases (e.g., relational, object-oriented, etc.), file systems, flat files, distributed datastores in which data is stored on more than one node of a computer network, peer-to-peer network datastores, or the like. In FIG. 14, an example datastore(s) may include, for example, historical data for previously identified products, purchase or order history, user profile information, and/or other information.

The processor(s) 1402 may be configured to access the memory 1404 and execute the computer-executable instructions loaded therein. For example, the processor(s) 1402 may be configured to execute the computer-executable instructions of the various program module(s), applications, engines, or the like of the electronic device(s) 1400 to cause or facilitate various operations to be performed in accordance with one or more embodiments of the disclosure. The processor(s) 1402 may include any suitable processing unit capable of accepting data as input, processing the input data in accordance with stored computer-executable instructions, and generating output data. The processor(s) 1402 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application-Specific Integrated Circuit (ASIC), a Field-Programmable Gate Array (FPGA), a System-on-a-Chip (SoC), a digital signal processor (DSP), and so forth. Further, the processor(s) 1402 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 1402 may be capable of supporting any of a variety of instruction sets.

Referring now to functionality supported by the various program module(s) depicted in FIG. 14, the update module(s) 1426 may include computer-executable instructions, code, or the like that are responsive to execution by one or more of the processor(s) 1402 may perform functions including, but not limited to, requesting and/or receiving software updates, such as over-the-air updates, requesting battery voltage data, storing data, modifying maximum battery charge values at integrated circuits, such as at a Power Management Integrated Circuit, controlling charging schemes and/or charging parameters, and the like.

The communication module(s) 1428 may include computer-executable instructions, code, or the like that are responsive to execution by one or more of the processor(s) 1402 may perform functions including, but not limited to, sending and/or receiving data, including content, sending and/or receiving instructions and commands, and the like.

The battery and charging module(s) 1430 may include computer-executable instructions, code, or the like that responsive to execution by one or more of the processor(s) 1402 may perform functions including, but not limited to, determining a charging voltage or other charging parameter, calculating elapsed time, calculating battery environment values, calculating acceleration or stress factors, calculating deceleration factors, adjusting charging voltages, determining predicted usage, determining voltage and/or temperature data, and the like.

Referring now to other illustrative components depicted as being stored in the data storage 1420, the O/S 1422 may be loaded from the data storage 1420 into the memory 1404 and may provide an interface between other application software executing on the electronic device(s) 1400 and the hardware resources of the electronic device(s) 1400. More specifically, the O/S 1422 may include a set of computer-executable instructions for managing the hardware resources of the electronic device(s) 1400 and for providing common services to other application programs (e.g., managing memory allocation among various application programs). In certain example embodiments, the O/S 1422 may control the execution of the other program module(s). The O/S 1422 may include any operating system now known or which may be developed in the future, including, but not limited to, any server operating system, any mainframe operating system, or any other proprietary or non-proprietary operating system.

The DBMS 1424 may be loaded into the memory 1404 and may support functionality for accessing, retrieving, storing, and/or manipulating data stored in the memory 1404 and/or data stored in the data storage 1420. The DBMS 1424 may use any of a variety of database models (e.g., relational model, object model, etc.) and may support any of a variety of query languages. The DBMS 1424 may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like. In those example embodiments in which the electronic device(s) 1400 is a mobile device, the DBMS 1424 may be any suitable lightweight DBMS optimized for performance on a mobile device.

Referring now to other illustrative components of the electronic device(s) 1400, the input/output (I/O) interface(s)

1406 may facilitate the receipt of input information by the electronic device(s) 1400 from one or more I/O devices as well as the output of information from the electronic device(s) 1400 to the one or more I/O devices. The I/O devices may include any of a variety of components, such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the electronic device(s) 1400 or may be separate. The I/O devices may further include, for example, any number of peripheral devices such as data storage devices, printing devices, and so forth.

The I/O interface(s) 1406 may also include an interface for an external peripheral device connection such as universal serial bus (USB), FireWire, Thunderbolt, Ethernet port or other connection protocol that may connect to one or more networks. The I/O interface(s) 1406 may also include a connection to one or more of the antenna(s) 1434 to connect to one or more networks via a wireless local area network (WLAN) (such as Wi-Fi) radio, Bluetooth, ZigBee, and/or a wireless network radio, such as a radio capable of communication with a wireless communication network such as a Long Term Evolution (LTE) network, WiMAX network, 3G network, a ZigBee network, etc.

The electronic device(s) 1400 may further include one or more network interface(s) 1408 via which the electronic device(s) 1400 may communicate with any of a variety of other systems, platforms, networks, devices, and so forth. The network interface(s) 1408 may enable communication, for example, with one or more wireless routers, one or more host servers, one or more web servers, and the like via one or more networks.

The antenna(s) 1434 may include any suitable type of antenna depending, for example, on the communications protocols used to transmit or receive signals via the antenna(s) 1434. Non-limiting examples of suitable antennas may include directional antennas, non-directional antennas, dipole antennas, folded dipole antennas, patch antennas, multiple-input multiple-output (MIMO) antennas, or the like. The antenna(s) 1434 may be communicatively coupled to one or more transceivers 1412 or radio components to which or from which signals may be transmitted or received.

As previously described, the antenna(s) 1434 may include a cellular antenna configured to transmit or receive signals in accordance with established standards and protocols, such as Global System for Mobile Communications (GSM), 3G standards (e.g., Universal Mobile Telecommunications System (UMTS), Wideband Code Division Multiple Access (W-CDMA), CDMA2000, etc.), 4G standards (e.g., Long-Term Evolution (LTE), WiMax, etc.), direct satellite communications, or the like.

The antenna(s) 1434 may additionally, or alternatively, include a Wi-Fi antenna configured to transmit or receive signals in accordance with established standards and protocols, such as the IEEE 802.11 family of standards, including via 2.4 GHz channels (e.g., 802.11b, 802.11g, 802.11n), 5 GHz channels (e.g., 802.11n, 802.11ac), or 60 GHz channels (e.g., 802.11 ad). In alternative example embodiments, the antenna(s) 1434 may be configured to transmit or receive radio frequency signals within any suitable frequency range, forming part of the unlicensed portion of the radio spectrum.

The antenna(s) 1434 may additionally, or alternatively, include a GNSS antenna configured to receive GNSS signals from three or more GNSS satellites carrying time-position information to triangulate a position therefrom. Such a GNSS antenna may be configured to receive GNSS signals from any current or planned GNSS such as, for example, the Global Positioning System (GPS), the GLONASS System, the Compass Navigation System, the Galileo System, or the Indian Regional Navigational System.

The transceiver(s) 1412 may include any suitable radio component(s) for—in cooperation with the antenna(s) 1434—transmitting or receiving radio frequency (RF) signals in the bandwidth and/or channels corresponding to the communications protocols utilized by the electronic device(s) 1400 to communicate with other devices. The transceiver(s) 1412 may include hardware, software, and/or firmware for modulating, transmitting, or receiving—potentially in cooperation with any of antenna(s) 1434—communications signals according to any of the communications protocols discussed above including, but not limited to, one or more Wi-Fi and/or Wi-Fi direct protocols, as standardized by the IEEE 802.11 standards, one or more non-Wi-Fi protocols, or one or more cellular communications protocols or standards. The transceiver(s) 1412 may further include hardware, firmware, or software for receiving GNSS signals. The transceiver(s) 1412 may include any known receiver and baseband suitable for communicating via the communications protocols utilized by the electronic device(s) 1400. The transceiver(s) 1412 may further include a low noise amplifier (LNA), additional signal amplifiers, an analog-to-digital (A/D) converter, one or more buffers, a digital baseband, or the like.

The sensor(s)/sensor interface(s) 1410 may include or may be capable of interfacing with any suitable type of sensing device, such as, for example, inertial sensors, force sensors, thermal sensors, photocells, and so forth. Example types of inertial sensors may include accelerometers (e.g., MEMS-based accelerometers), gyroscopes, and so forth.

The camera(s) 1414 may be any device configured to capture ambient light or images. The microphone(s) 1414 may be any device configured to receive analog sound input or voice data. The rechargeable batter(ies) 1416 may be any suitable power storage device, such as a lithium-ion battery, and may be in various form factors, such as pouch form factors, cylindrical form factors, and the like.

It should be appreciated that the program module(s), applications, computer-executable instructions, code, or the like depicted in FIG. 14 as being stored in the data storage 1420 are merely illustrative and not exhaustive and that processing described as being supported by any particular module may alternatively be distributed across multiple module(s) or performed by a different module. In addition, various program module(s), script(s), plug-in(s), Application Programming Interface(s) (API(s)), or any other suitable computer-executable code hosted locally on the electronic device(s) 1400, and/or hosted on other computing device(s) accessible via one or more networks, may be provided to support functionality provided by the program module(s), applications, or computer-executable code depicted in FIG. 14 and/or additional or alternate functionality. Further, functionality may be modularized differently such that processing described as being supported collectively by the collection of program module(s) depicted in FIG. 14 may be performed by a fewer or greater number of module(s), or functionality described as being supported by any particular module may be supported, at least in part, by another module. In addition, program module(s) that support the functionality described herein may form part of one or more applications executable across any number of systems or devices in accordance with any suitable computing model such as, for example, a client-server model, a peer-to-peer model, and so forth. In addition, any of the functionality described as being supported by any of the program module(s) depicted in FIG. 14 may be implemented, at least partially, in hardware and/or firmware across any number of devices.

It should further be appreciated that the electronic device(s) 1400 may include alternate and/or additional hardware, software, or firmware components beyond those described or depicted without departing from the scope of the disclosure. More particularly, it should be appreciated that software, firmware, or hardware components depicted as forming part of the electronic device(s) 1400 are merely illustrative and that some components may not be present or additional components may be provided in various embodiments. While various illustrative program module(s) have been depicted and described as software module(s) stored in the data storage 1420, it should be appreciated that functionality described as being supported by the program module(s) may be enabled by any combination of hardware, software, and/or firmware. It should further be appreciated that each of the above-mentioned module(s) may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular module may, in various embodiments, be provided at least in part by one or more other module(s). Further, one or more depicted module(s) may not be present in certain embodiments, while in other embodiments, additional module(s) not depicted may be present and may support at least a portion of the described functionality and/or additional functionality. Moreover, while certain module(s) may be depicted and described as sub-module(s) of another module, in certain embodiments, such module(s) may be provided as independent module(s) or as sub-module(s) of other module(s).

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language, such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software components without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines, and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages but may invoke software components written in another programming language.

Computer-executable program instructions may be loaded onto a special-purpose computer or other particular machines, a processor, or other programmable data processing apparatus to produce a particular machines, such that execution of the instructions on the computer, processor, or other programmable data processing apparatus causes one or more functions or operations specified in the flow diagrams to be performed. These computer program instructions may also be stored in a computer-readable storage medium (CRSM) that, upon execution, may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

That which is claimed is:

1. A PCR testing module, comprising:
   a main cabinet comprising an enclosure that houses a PCR machine;
   a patient interface disposed on an exterior of the main cabinet, the patient interface configured to accept input from a user;
   a sample input station accessible at the exterior of the main cabinet, the sample input station being configured to receive a sample collection device (SCD) comprising a saliva sample;
   a barcode scanner configured to read a barcode on the SCD;
   an oven within the enclosure configured to thermally lyse the saliva sample in the SCD;
   an SCD processing mechanism configured to transfer a lysed microportion of the saliva sample and water into a PCR sample tube that comprises a lyophilized master mix;
   a sonicator configured to ultrasonically mix the lysed microportion of the saliva sample, the water, and the lyophilized master mix in the PCR sample tube attached to the SCD;
   a robotic manipulator configured to (i) separate the PCR sample tube from the SCD and discard the SCD into a biohazard waste bin within the cabinet, (ii) seal the PCR sample tube to output a sealed PCR tube, and (iii) transfer the sealed PCR sample tube to the PCR machine; and
   a controller configured to:
      cause the PCR machine to conduct a PCR test on the contents of the PCR sample tube;
      determine a result of the PCR test; and
      provide results of the PCR test.

2. The PCR testing module of claim 1, wherein the PCR machine comprises a continuous PCR system comprising:
   a sample scanner configured to read a bar code on the PCR sample tube;
   a conveyor system for moving a plurality of received PCR sample tubes through heating and cooling zones within the PCR machine; and
   an array of laser diodes and photodetectors to detect the fluorescent intensity in each PCR sample tube,
   wherein the conveyor system is configured to eject the PCR sample tube into the biohazard bin upon completion of testing.

3. The PCR testing module of claim 1, wherein the main cabinet further comprises:
   a disposal bay door for accessing the biohazard waste bin;
   a maintenance access door for accessing an electrical cabinet;
   a HEPA filter, and
   an exhaust port configured to exhaust air from the enclosure after passing through the HEPA filter.

4. A testing module, comprising:
   a housing having a PCR machine disposed therein;
   an input station on the housing, wherein the input station is configured to receive a sample collection device (SCD) comprising a biological specimen sample;
   an SCD processing mechanism configured to transfer a lysed microportion of the biological specimen sample into a PCR sample tube;
   at least one mechanism configured to transfer the PCR sample tube to the PCR machine; and
   a controller configured to cause the PCR machine to (i) conduct a PCR test on the contents of the PCR sample tube, and (ii) generate results of the PCR test.

5. The testing module of claim 4, further comprising an input interface disposed on the housing, the input interface configured to accept input associated with conducting the PCR test.

6. The testing module of claim 4, further comprising a first scanner configured to read a first machine-readable code on the SCD and a second scanner configured to read a second machine-readable code on the PCR sample tube.

7. The testing module of claim 4, further comprising a heater configured to lyse the biological specimen sample in the SCD.

8. The testing module of claim 4, further comprising a sonicator configured to ultrasonically mix the lysed microportion of the biological specimen sample with other materials in the PCR sample tube.

9. The testing module of claim 4, further comprising a mechanism configured to separate the PCR sample tube from the SCD.

10. The testing module of claim 4, further comprising:
    a conveyor system configured to move a plurality of PCR sample tubes through heating and cooling zones within the PCR machine;
    a sample scanner configured to read a machine-readable code on each of the plurality of PCR sample tubes; and
    an array of laser diodes and photodetectors to detect the fluorescent intensity in each of the plurality of PCR sample tubes.

11. The testing module of claim 4, further comprising:
    a robotic manipulator configured to separate the biological specimen sample from a swab within the SCD.

12. The testing module of claim 4, further comprising:
    a sealing machine configured to apply a film or closure over an opening of the PCR sample tube.

13. The testing module of claim 4, wherein the housing further comprises:
    a biohazard bin positioned to receive the PCR sample tube upon completion of the PCR test; and
    a disposal bay door for accessing the biohazard waste bin.

14. The testing module of claim 4, wherein the housing further comprises:
    a HEPA filter, and
    an exhaust port configured to exhaust air from the housing after passing through the HEPA filter.

15. The testing module of claim 4, wherein the PCR machine comprises a continuous PCR system.

16. The testing module of claim 15, wherein the continuous PCR machine comprises:
a track;
a plurality of stationary thermal holders disposed along the track which are configured to expose the PCR sample tube to thermal cycles; and
a conveyor belt configured to convey the PCR sample tube among the plurality of stationary thermal holders.

17. The testing module of claim 16, wherein the continuous PCR machine further comprises:
one or more sensors configured to detect fluorescent intensity in the PCR sample tube as the PCR sample tube undergoes thermal cycling; and
vacuum grippers configured to move the PCR sample tube to, along, and from the track.

18. The testing module of claim 4, further comprising:
a user interface configured to accept payment for the test, to identify the user, and/or to output test results.

19. A testing module, comprising:
a housing having a PCR machine disposed therein;
an input station on the housing, wherein the input station is configured to receive a sample collection device (SCD) comprising a biological specimen sample;
a robotic manipulator configured to separate the biological specimen sample from a swab within the SCD;
an SCD processing mechanism configured to transfer a lysed microportion of the biological specimen sample into a PCR sample tube;
at least one mechanism configured to transfer the PCR sample tube to the PCR machine; and
a controller configured to cause the PCR machine to (i) conduct a PCR test on the contents of the PCR sample tube, and (ii) generate results of the PCR test.

20. The testing module of claim 19, further comprising:
a first scanner configured to read a first machine-readable code on the SCD;
a second scanner configured to read a second machine-readable code on the PCR sample tube;
a mechanism configured to separate the PCR sample tube from the SCD; and
a sealing machine configured to apply a film or closure over an opening of the separated PCR sample tube.

* * * * *